US007326256B2

(12) United States Patent
Cottard et al.

(10) Patent No.: US 7,326,256 B2
(45) Date of Patent: Feb. 5, 2008

(54) COMPOSITION FOR THE OXIDATION DYEING OF KERATIN FIBERS, COMPRISING AT LEAST ONE NON-OXYALKENYLATED FATTY ALCOHOL, AT LEAST ONE OXIDATION DYE, AT LEAST ONE ASSOCIATIVE POLYMER, AND AT LEAST ONE AMIDE OF AN ALKANOLAMINE AND A $C_{14}$-$C_{30}$ FATTY ACID

(75) Inventors: François Cottard, Courbevoie (FR); Christine Rondeau, Sartrouville (FR)

(73) Assignee: L'Oréal S.A., Paris (FR)

( * ) Notice: Subject to any disclaimer, the term of this patent is extended or adjusted under 35 U.S.C. 154(b) by 81 days.

(21) Appl. No.: 10/728,888

(22) Filed: Dec. 8, 2003

(65) Prior Publication Data

US 2004/0205902 A1 Oct. 21, 2004

Related U.S. Application Data

(60) Provisional application No. 60/502,618, filed on Sep. 15, 2003.

(30) Foreign Application Priority Data

Dec. 6, 2002 (FR) .................................. 02 15476

(51) Int. Cl.
*A61K 7/13* (2006.01)
(52) U.S. Cl. .................... 8/405; 8/406; 8/408; 8/409; 8/410; 8/411; 8/412; 8/552; 8/554; 8/555; 8/558
(58) Field of Classification Search ............ 8/405, 8/406, 408, 409, 410, 411, 412, 552, 554, 8/555, 558
See application file for complete search history.

(56) References Cited

U.S. PATENT DOCUMENTS

| 2,261,002 | A | 10/1941 | Ritter .......................... 260/570 |
| 2,271,378 | A | 1/1942 | Searle .......................... 167/72 |
| 2,273,780 | A | 2/1942 | Dittmar ........................ 260/28 |
| 2,375,853 | A | 5/1945 | Kirby et al. ................. 260/983 |
| 2,388,614 | A | 11/1945 | Kirby et al. ................... 167/22 |
| 2,454,547 | A | 11/1948 | Bock et al. ............... 260/567.6 |
| 2,528,378 | A | 10/1950 | Mannheimer ............... 260/309.6 |
| 2,781,354 | A | 2/1957 | Mannheimer ............... 260/309.6 |
| 2,961,347 | A | 11/1960 | Floyd .......................... 117/141 |
| 3,206,462 | A | 9/1965 | McCarty ................... 260/256.4 |
| 3,227,615 | A | 1/1966 | Korden ....................... 167/87.1 |
| 3,472,840 | A | 10/1969 | Stone et al. ................. 260/231 |
| 3,632,559 | A | 1/1972 | Matter et al. ................. 260/78 |
| 3,836,537 | A | 9/1974 | Boerwinkle et al. ....... 260/29.6 |
| 3,874,870 | A | 4/1975 | Green et al. .................. 71/67 |
| 3,879,376 | A | 4/1975 | Vanlerberghe et al. ...... 260/211 |
| 3,910,862 | A | 10/1975 | Barabas et al. ............ 260/79.3 |
| 3,912,808 | A | 10/1975 | Sokol ........................... 424/71 |
| 3,915,921 | A | 10/1975 | Schlatzer ................... 260/17.4 |
| 3,917,817 | A | 11/1975 | Vanlerberghe et al. ......... 424/70 |
| 3,929,990 | A | 12/1975 | Green et al. ................... 424/78 |
| 3,966,904 | A | 6/1976 | Green et al. ................... 424/78 |
| 4,001,432 | A | 1/1977 | Green et al. ................. 424/329 |
| 4,005,193 | A | 1/1977 | Green et al. ................. 424/168 |
| 4,013,787 | A | 3/1977 | Varlerberghe et al. ......... 424/70 |
| 4,025,617 | A | 5/1977 | Green et al. ................... 424/78 |
| 4,025,627 | A | 5/1977 | Green et al. ............. 424/248.4 |
| 4,025,653 | A | 5/1977 | Green et al. ................. 424/329 |
| 4,026,945 | A | 5/1977 | Green et al. ................. 260/567 |
| 4,027,020 | A | 5/1977 | Green et al. ........... 424/248.56 |
| 4,031,307 | A | 6/1977 | DeMartino et al. ......... 536/114 |
| 4,075,136 | A | 2/1978 | Schaper ..................... 260/2 R |
| 4,131,576 | A | 12/1978 | Iovine et al. ............... 260/17.4 |
| 4,157,388 | A | 6/1979 | Christiansen ................ 424/70 |
| 4,165,367 | A | 8/1979 | Chakrabarti ................. 424/47 |
| 4,166,894 | A | 9/1979 | Schaper ..................... 528/271 |
| 4,172,887 | A | 10/1979 | Vanlerberghe et al. ........ 424/70 |
| RE30,199 | E | 1/1980 | Rose et al. ................... 8/10.2 |
| 4,189,468 | A | 2/1980 | Vanlerberghe et al. ........ 424/70 |
| 4,217,914 | A | 8/1980 | Jacquet et al. ................. 132/7 |
| 4,223,009 | A | 9/1980 | Chakrabarti ................. 424/47 |
| 4,240,450 | A | 12/1980 | Grollier et al. ................ 132/7 |
| 4,277,581 | A | 7/1981 | Vanlerberghe et al. ...... 525/420 |
| 4,349,532 | A | 9/1982 | Vanlerberghe et al. ........ 424/47 |
| 4,357,141 | A * | 11/1982 | Grollier et al. ................ 8/406 |
| 4,381,919 | A | 5/1983 | Jacquet et al. ................ 8/405 |
| 4,390,689 | A | 6/1983 | Jacquet et al. .............. 528/335 |
| 4,509,949 | A | 4/1985 | Huang et al. ................ 586/558 |
| 4,591,610 | A | 5/1986 | Grollier ....................... 524/55 |
| 4,702,906 | A | 10/1987 | Jacquet et al. ................ 424/70 |

(Continued)

FOREIGN PATENT DOCUMENTS

DE 23 59 399 6/1975

(Continued)

OTHER PUBLICATIONS

M.R. Porter, "Handbook of Surfactants," published by Blackie & Son, 1991, pp. 116-178.

(Continued)

*Primary Examiner*—Eisa Elhilo
(74) *Attorney, Agent, or Firm*—Finnegan, Henderson, Farabow, Garrett & Dunner, LLP

(57) ABSTRACT

Disclosed herein is a composition for the oxidation dyeing of keratin fibers, for example of human keratin fibers such as the hair, comprising, in a medium suitable for dyeing,
a) at least one oxidation dye;
b) at least one non-oxyalkylenated fatty alcohol;
c) at least one associative polymer; and
d) at least one amide of an alkanolamine and a $C_{14}$-$C_{30}$ fatty acid.

79 Claims, No Drawings

U.S. PATENT DOCUMENTS

| | | | |
|---|---|---|---|
| 4,719,282 A | 1/1988 | Nadolsky et al. | 528/310 |
| 4,761,273 A | 8/1988 | Grollier et al. | 424/47 |
| 4,839,166 A | 6/1989 | Grollier et al. | 424/71 |
| 4,948,579 A | 8/1990 | Jacquet et al. | 424/72 |
| 4,996,059 A | 2/1991 | Grollier et al. | 424/71 |
| 5,061,289 A | 10/1991 | Clausen et al. | 8/405 |
| 5,089,252 A | 2/1992 | Grollier et al. | 424/47 |
| 5,196,189 A | 3/1993 | Jacquet et al. | 424/72 |
| 5,380,340 A | 1/1995 | Neunhoeffer et al. | 8/409 |
| 5,478,562 A | 12/1995 | Cauwet et al. | 474/401 |
| 5,534,036 A | 7/1996 | Junino et al. | 8/411 |
| 5,534,267 A | 7/1996 | Neunhoeffer et al. | 424/701 |
| 5,663,366 A | 9/1997 | Neunhoeffer et al. | 548/371.4 |
| 5,766,576 A | 6/1998 | Löwe et al. | 424/62 |
| 5,807,957 A | 9/1998 | Samour et al. | 528/49 |
| 5,876,463 A | 3/1999 | Garcia et al. | 8/405 |
| 6,099,592 A | 8/2000 | Vidal et al. | 8/409 |
| 6,284,003 B1 | 9/2001 | Rose et al. | 8/412 |
| 6,287,578 B1 | 9/2001 | Duetsch et al. | 424/401 |
| 6,338,741 B1 | 1/2002 | Vidal et al. | 8/409 |
| 6,436,151 B2 | 8/2002 | Cottard et al. | 8/406 |
| 6,645,258 B2 | 11/2003 | Vidal et al. | 8/405 |
| 6,677,304 B2 | 1/2004 | DiNapoli | 514/9 |
| 2001/0023514 A1* | 9/2001 | Cottard et al. | 8/406 |
| 2001/0023515 A1 | 9/2001 | Cottard et al. | 8/406 |
| 2001/0041671 A1 | 11/2001 | Napoli | 514/9 |
| 2002/0046431 A1* | 4/2002 | Laurent et al. | 8/405 |
| 2002/0050013 A1 | 5/2002 | Vidal et al. | 8/405 |
| 2002/0119171 A1 | 8/2002 | Gruning et al. | 424/401 |
| 2003/0019051 A9 | 1/2003 | Vidal et al. | 8/405 |
| 2003/0093866 A1 | 5/2003 | Vidal et al. | 8/405 |
| 2003/0124079 A1 | 7/2003 | Mougin et al. | 424/70.11 |
| 2004/0019981 A1 | 2/2004 | Cottard et al. | 8/405 |
| 2004/0049861 A1 | 3/2004 | Cottard et al. | 8/405 |
| 2004/0106546 A1 | 6/2004 | Napoli | 514/11 |
| 2004/0141943 A1 | 7/2004 | Mougin et al. | 424/70.17 |

FOREIGN PATENT DOCUMENTS

| | | |
|---|---|---|
| DE | 38 43 892 A1 | 6/1990 |
| DE | 41 33 957 A1 | 4/1993 |
| DE | 195 43 988 | 5/1997 |
| EP | 0 080 976 | 6/1983 |
| EP | 0 122 324 | 10/1984 |
| EP | 0 173 109 | 3/1986 |
| EP | 0 337 354 A1 | 10/1989 |
| EP | 0 216 479 | 2/1991 |
| EP | 0 591 059 A1 | 4/1994 |
| EP | 0 767 191 A2 | 4/1997 |
| EP | 0 824 914 A1 | 2/1998 |
| EP | 0 825 200 A1 | 2/1998 |
| EP | 0 884 344 A2 | 12/1998 |
| EP | 0 959 090 A1 | 11/1999 |
| EP | 0 959 091 A1 | 11/1999 |
| EP | 0 959 094 A1 | 11/1999 |
| EP | 1 142 555 | 10/2001 |
| EP | 1 142 566 A1 | 10/2001 |
| FR | 1 400 366 | 5/1965 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 137 684 | 12/1972 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 402 446 | 4/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| FR | 2 811 993 | 1/2002 |
| GB | 1 021 400 | 3/1966 |
| GB | 1 026 978 | 4/1966 |
| GB | 1 153 196 | 5/1969 |
| GB | 1 394 353 | 5/1975 |
| JP | 1988-169571 | 1/1990 |
| JP | 09010659 A | 1/1997 |
| WO | WO 94/08969 | 4/1994 |
| WO | WO 94/08970 | 4/1994 |
| WO | WO 96/15765 | 5/1996 |
| WO | WO 97/24105 | 7/1997 |
| WO | WO 97/24106 | 7/1997 |
| WO | WO 97/24107 | 7/1997 |
| WO | WO 98/27941 | 7/1998 |
| WO | WO 98/44012 | 10/1998 |
| WO | WO 99/36047 A2 | 7/1999 |
| WO | WO 01/68043 A3 | 9/2001 |
| WO | WO 02/38115 A1 | 5/2002 |
| WO | WO 02/45651 A2 | 6/2002 |

OTHER PUBLICATIONS

G. Fonnum, et al. "Associative Thickeners, Part I: Synthesis, rheology and aggregation behavior," Collid Plymn. Sci. 271 pp. 380-389 (1993).
French Search Report dated Aug. 26, 2003.
European Patent Office Search Report dated May 24, 2004.
International Search Report dated May 20, 1999.
International Search Report dated Mar. 26, 2002.
English language Derwent Abstract for JP 1988-169571, published Jan. 23, 1990.

* cited by examiner

COMPOSITION FOR THE OXIDATION DYEING OF KERATIN FIBERS, COMPRISING AT LEAST ONE NON-OXYALKENYLATED FATTY ALCOHOL, AT LEAST ONE OXIDATION DYE, AT LEAST ONE ASSOCIATIVE POLYMER, AND AT LEAST ONE AMIDE OF AN ALKANOLAMINE AND A $C_{14}$-$C_{30}$ FATTY ACID

This application claims benefit of U.S. Provisional Application No. 60/502,619, filed Sep. 15, 2003.

Disclosed herein is a composition for the oxidation dyeing of keratin fibers, for example human keratin fibers, such as the hair, comprising at least one oxidation dye, at least one non-oxyalkylenated fatty alcohol, at least one associative polymer, and at least one amide of an alkanolamine and of a $C_{14}$-$C_{30}$ fatty acid.

It is known practice to dye keratin fibers, such as human hair, with dye compositions comprising oxidation dye precursors, generally known as "oxidation bases", such as ortho- and para-phenylenediamines, ortho- and para-aminophenols, and heterocyclic bases.

Oxidation dye precursors are compounds that are initially uncolored or only weakly colored, which develop their dyeing power on the hair in the presence of oxidizing agents, leading to the formation of colored compounds. The formation of these colored compounds may result either from an oxidative condensation of the oxidation bases with themselves or from an oxidative condensation of the oxidation bases with coloration modifiers, or "couplers", which may be present in the dye compositions used in oxidation dyeing and may be represented for example by meta-phenylenediamines, meta-aminophenols, meta-diphenols, and certain heterocyclic compounds.

The variety of molecules used, which comprise on the one hand the oxidation bases and on the other hand the couplers, may allow a wide range of colors to be obtained.

Compositions which comprise oxidation dyes and are mixed before use with an oxidizing agent may be in the form of water-based creams conventionally comprising fatty alcohols and occasionally soaps or associative polymers. These creams may have a high fatty alcohol content in order to ensure the consistency and stability of the medium.

The present inventors, however, have noted that these dye compositions may exhibit a change in viscosity over time, which may be manifested in a reduction in the ease of mixing with the oxidizing agent or in an impairment of the surface qualities.

However, following substantial research carried out into the question, the present inventors have found that oxidation dye compositions comprising at least one oxidation dye, at least one non-oxyalkylenated fatty alcohol, at least one associative polymer, and at least one amide of an alkanolamine and a $C_{14}$-$C_{30}$ fatty acid may have a satisfactory consistency and a viscosity which may be stable over time without the need to raise the concentration of fatty alcohol.

Accordingly, disclosed herein is a composition for the oxidation dyeing of keratin fibers, for example human keratin fibres such as the hair, comprising, in a medium suitable for dyeing, a) at least one oxidation dye;
b) at least one non-oxyalkylenated fatty alcohol;
c) at least one associative polymer; and
d) at least one amide of an alkanolamine and a $C_{14}$-$C_{30}$ fatty acid.

Also disclosed herein is a ready-to-use composition for the dyeing of keratin fibers which comprises at least one oxidation dye, at least one non-oxyalkylenated fatty alcohol, at least one associative polymer, at least one amide of an alkanolamine and a $C_{14}$-$C_{30}$ fatty acid, and at least one oxidizing agent.

As used herein, the expression "ready-to-use composition" means the composition intended for application as it is to the keratin fibers; that is to say, the composition may be stored as it is before use or may result from mixing of at least two compositions.

Also disclosed herein is a process for the oxidation dyeing of keratin fibers, for example human keratin fibers such as the hair, comprising applying to the fibers a composition (A) comprising, in a medium suitable for dyeing, at least one oxidation dye, at least one non-oxyalkylenated fatty alcohol, at least one associative polymer, and at least one amide of an alkanolamine and a $C_{14}$-$C_{30}$ fatty acid, wherein the color is developed at alkaline, neutral, or acidic pH, by means of a composition (B) comprising at least one oxidizing agent, which is mixed with the composition (A) at the moment of use or which is applied sequentially without intermediate rinsing.

Yet another embodiment provides multi-compartment dyeing devices or multi-compartment kits for the oxidation dyeing of keratin fibers, for example human keratin fibers such as the hair. A device according to the present disclosure may comprise a first compartment comprising at least one oxidation dye, at least one non-oxyalkylenated fatty alcohol, at least one associative polymer, and at least one amide of an alkanolamine and a $C_{14}$-$C_{30}$ fatty acid, and a second compartment comprising at least one oxidizing agent.

Other features, aspects, subjects, and advantages of the present disclosure will emerge even more clearly on reading the description and the examples that follow.

The at least one amide of an alkanolamine and a $C_{14}$-$C_{30}$ fatty acid may be chosen from the amides of a $C_2$-$C_{10}$ alkanolamine and a $C_{14}$-$C_{30}$ fatty acid, such as from the amides of a $C_2$-$C_{10}$ alkanolamine and a $C_{14}$-$C_{22}$ fatty acid.

The at least one amide of an alkanolamine and a $C_{14}$-$C_{30}$ fatty acid may, for example, be chosen from:

oleic acid diethanolamide, such as the amide sold under the trade name MEXANYL® GT by the company Chimex;

myristic acid monoethanolamide, such as the amide sold under the trade name COMPERLAN® MM by the company Cognis;

soya fatty acids diethanolamide, such as the amide sold under the trade name COMPERLAN® VOD by the company Cognis;

stearic acid ethanolamide, such as the amide sold under the trade name MONAMID® S by the company Uniqema;

oleic acid monoisopropanolamide, such as the amide sold under the trade name WITCAMIDE® 61 by the company Witco;

linoleic acid diethanolamide, such as the amide sold under the trade name PURTON® SFD by the company Zschimmer Schwarz;

stearic acid monoethanolamide, such as the amide sold under the trade name MONAMID® 972 by the company ICI/Uniqema;

behenic acid monoethanolamide, such as the amide sold under the trade name INCROMIDE® BEM from Croda;

isostearic acid monoisopropanolamide, such as the amide sold under the trade name WITCAMIDE® SPA by the company Witco;

erucic acid diethanolamide, such as the amide sold by the company Stearineries Dubois; and ricinoleic acid monoethanolamide, such as the amide sold by the company Stearineries Dubois.

The at least one amide of an alkanolamine and a $C_{14}$-$C_{30}$ fatty acid may be present in the composition in proportions ranging from 0.1% to 10%, such as from 1% to 5%, by weight relative to the total weight of the composition.

The at least one non-oxyalkylenated fatty alcohol disclosed herein can be chosen from at least one of saturated, unsaturated, linear, and branched non-oxyalkylenated fatty alcohols.

As an example, these fatty alcohols may be $C_{12}$-$C_{22}$ alcohols.

Among these fatty alcohols, mention may be made of lauryl, cetyl, stearyl, oleyl, behenyl, linoleyl, undecylenyl, palmitoleyl, arachidonyl, and erucyl alcohols and mixtures thereof.

The non-oxyalkylenated fatty alcohol may be present in the composition in proportions ranging from 0.1% to 20%, for example from 1% to 10%, by weight relative to the total weight of the composition.

The at least one oxidation dye that may be used according to certain embodiments may be chosen from oxidation bases and couplers.

The composition disclosed herein may comprise at least one oxidation base.

The oxidation bases that may be used in the context of certain embodiments may be chosen from those conventionally used in oxidation dyeing, and among which mention may be made of ortho- and para-phenylenediamines, double bases, ortho- and para-aminophenols, heterocyclic bases, and the acid addition salts thereof.

Mention may also be made of:
(I) the para-phenylenediamines of formula (I) below, and the acid addition salts thereof:

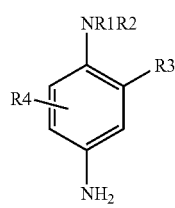

(I)

in which:

R1 is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals, and $C_1$-$C_4$ alkyl radicals substituted with at least one of nitrogenous, phenyl, and 4'-aminophenyl groups;

R2 is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals, and $C_1$-$C_4$ alkyl radicals substituted with at least one nitrogenous group;

R1 and R2 may also form, together with the nitrogen atom to which they are attached, a 5- or 6-membered nitrogen heterocycle optionally substituted with at least one of alkyl, hydroxyl, and ureido groups;

R3 is chosen from a hydrogen atom, halogen atoms such as chlorine, $C_1$-$C_4$ alkyls, sulpho radicals, a carboxyl radical, $C_1$-$C_4$ monohydroxyalkyl radicals, $C_1$-$C_4$ hydroxyalkoxy radicals, acetylamino($C_1$-$C_4$)alkoxy radicals, mesylamino ($C_1$-$C_4$)alkoxy radicals, and carbamoylamino($C_1$-$C_4$)alkoxy radicals; and R4 is chosen from a hydrogen atom, halogen atoms, and $C_1$-$C_4$ alkyls.

Among the nitrogenous groups of formula (I) above, mention may be made of amino, mono($C_1$-$C_4$)alkylamino, di($C_1$-$C_4$)alkylamino, tri($C_1$-$C_4$)alkylamino, monohydroxy ($C_1$-$C_4$)alkylamino, imidazolinium, and ammonium radicals.

Among the para-phenylenediamines of formula (I) above, mention may be made of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-N,N-bis(β-hydroxyethyl)-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,β-dihydroxypropyl)-para-phenylenediamine, N-(4'-aminophenyl)-para-phenylenediamine, N-phenyl-para-phenylenediamine and 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and the acid addition salts thereof.

Among the para-phenylenediamines of formula (I) above, mention may also be made of, for example, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the acid addition salts thereof.

(II) As used herein, the term double bases means compounds comprising at least two aromatic nuclei having at least one of amino and hydroxyl groups.

Among the double bases that can be used as oxidation bases in the dye compositions disclosed herein, mention may be made of the compounds corresponding to formula (II) below, and the acid addition salts thereof:

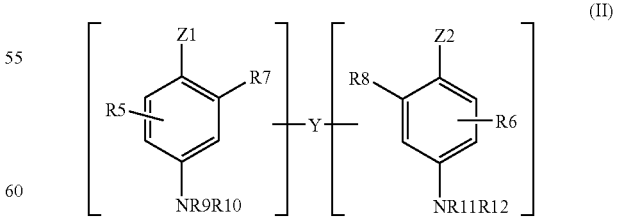

(II)

in which:

Z1 and Z2, which may be identical or different, are chosen from hydroxyl radicals and —$NH_2$ radicals, optionally substituted with at least one of $C_1$-$C_4$ alkyl radicals and a linker arm Y;

the linker arm Y is chosen from linear and branched alkylene chains having from 1 to 14 carbon atoms, optionally interrupted by and optionally terminated with at least one of nitrogenous groups and heteroatoms such as oxygen, sulphur, and nitrogen atoms, and optionally substituted with at least one of hydroxyl and $C_1$-$C_6$ alkoxy radicals;

R5 and R6 are chosen from a hydrogen atom, halogen atoms, $C_1$-$C_4$ alkyls, $C_1$-$C_4$ monohydroxyalkyls, $C_2$-$C_4$ polyhydroxyalkyls, $C_1$-$C_4$ aminoalkyls, and a linker arm Y; and R7, R8, R9, R10, R11 and R12, which may be identical or different, are chosen from a hydrogen atom, a linker arm Y, and $C_1$-$C_4$ alkyl radicals;

it being understood that the compounds of formula (II) comprise only one linker arm Y per molecule.

Among the nitrogenous groups of formula (II) above, mention may be made of amino, mono($C_1$-$C_4$)alkylamino, di($C_1$-$C_4$)alkylamino, tri($C_1$-$C_4$)alkylamino, monohydroxy ($C_1$-$C_4$)alkylamino, imidazolinium, and ammonium radicals.

Among the double bases of formula (II) above, mention may also be made of N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis-(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the acid addition salts thereof.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane, or one of the acid addition salts thereof, may, for example, be used.

(III) the para-aminophenols corresponding to formula (III) below, and the acid addition salts thereof:

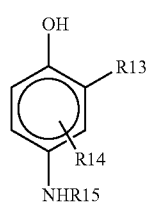

(III)

in which:

R13 is chosen from a hydrogen atom, halogen such as fluorine, $C_1$-$C_4$ alkyl, $C_1$-$C_4$ monohydroxyalkyl, ($C_1$-$C_4$) alkoxy($C_1$-$C_4$)alkyl, $C_1$-$C_4$ aminoalkyl, and hydroxy($C_1$-$C_4$) alkylamino($C_1$-$C_4$)alkyl radicals.

R14 is chosen from a hydrogen atom, halogen such as fluorine, $C_1$-$C_4$ alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl, and ($C_1$-$C_4$)alkoxy-($C_1$-$C_4$)alkyl radicals.

R15 is chosen from a hydrogen atom and $C_1$-$C_4$ alkyl radicals.

Among the para-aminophenols of formula (III) above, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

(IV) the ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

(V) among the heterocyclic bases that can be used as oxidation bases in the dye compositions in accordance with certain embodiments, mention may be made of pyridine derivatives, pyrimidine derivatives, pyrazole derivatives, and the acid addition salts thereof.

Among the pyridine derivatives, mention may also be made of the compounds described, for example, in patents GB 1 026 978 and GB 1 153 196, as well as the compounds 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the acid addition salts thereof.

Among the pyrimidine derivatives, mention may also be made of the compounds described, for example, in German patent DE 2 359 399, Japanese patents JP 88-169 571 and JP 91-10659, and patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol; 5,6-dimethyl-pyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine, 3-amino-5-methyl-7-imidazolylpropylamino-pyrazolo[1,5-a]pyrimidine, and the acid addition salts thereof and the tautomeric forms thereof, when a tautomeric equilibrium exists.

Among the pyrazole derivatives, mention may also be made the compounds described in patents DE 3 843 892, DE 4 133 957 and patent applications WO 94/08969, WO 94/08970, FR-A-2 733 749, and DE 195 43 988, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)

amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the acid addition salts thereof.

According to certain embodiments, the oxidation bases may be present in an amount ranging from 0.0005% to 12% by weight relative to the total weight of the composition, such as from 0.005% to 8% by weight relative to the total weight of the composition.

The couplers that may be used in the dyeing method disclosed herein include those conventionally used in oxidation dye compositions, that is to say meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, and the acid addition salts thereof.

These couplers may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, and the acid addition salts thereof.

When they are present, these couplers may be present in an amount ranging from 0.0001% to 10% by weight relative to the total weight of the composition, such as from 0.005% to 5% by weight relative to the total weight of the composition.

In general, the acid addition salts of the oxidation bases and couplers may be chosen from hydrochlorides, hydrobromides, sulphates, tartrates, lactates, and acetates.

The composition disclosed herein may also comprise at least one direct dye, in addition to the at least one oxidation dye defined above, in order to enrich the shades with glints. This at least one direct dye may be chosen from neutral, cationic, and anionic nitro dyes, azo dyes, and anthraquinone dyes, and may be present in an amount ranging from 0.001% to 20%, such as from 0.01% to 10%, by weight relative to the total weight of the composition.

The at least one associative polymer may be a polymer whose molecules are capable, in the formulation medium, of undergoing association with another associative polymer or with molecules of other compounds.

In one embodiment, the at least one associative polymer is an amphiphilic polymer, i.e., a polymer comprising at least one hydrophilic moiety which renders the polymer soluble in water and at least one hydrophobic region, comprising at least one fatty chain, by means of which the polymer interacts and undergoes assembly with another associative polymer or with other molecules.

The at least one associative polymer disclosed herein may be chosen from non-ionic, anionic, cationic, and amphoteric associative polymers.

The at least one associative polymers disclosed herein may, for example, be chosen from associative polymers comprising at least one fatty chain. The fatty chain may have from 8 to 30 carbon atoms, such as from 10 to 30 carbon atoms.

Among the anionic associative polymers comprising at least one fatty chain, mention may be made of:

(I) anionic associative polymers comprising at least one hydrophilic unit and at least one fatty-chain allyl ether unit, such as those whose hydrophilic unit comprises an ethylenic unsaturated anionic monomer, such as vinylcarboxylic acid, acrylic acid, methacrylic acid, and mixtures thereof, wherein the fatty-chain allyl ether unit of which corresponds to the monomer of formula (IV) below:

CH$_2$=CR'CH$_2$OB$_n$R  (IV)

in which

R' is chosen from a hydrogen atom and CH$_3$;

B is an ethyleneoxy radical;

n is an integer ranging from 0 to 100;

R is a hydrocarbon-based radical chosen from alkyl, arylalkyl, aryl, alkylaryl, and cycloalkyl radicals, having from 8 to 30 carbon atoms, such as from 10 to 24 carbon atoms, or from 12 to 18 carbon atoms. A unit of formula (I) that may be mentioned is a unit in which R' is a hydrogen atom, n is equal to 10, and R is a stearyl (C$_{18}$) radical.

Anionic amphiphilic polymers of this type are described and prepared, for example, according to an emulsion polymerization process in patent EP 0 216 479.

Among these fatty-chain anionic associative polymers, those that may be mentioned according certain embodiments are polymers formed from at least one of 20% to 60% by weight of acrylic acid and methacrylic acid, from 5% to 60% by weight of at least one lower alkyl (meth)acrylate, from 2% to 50% by weight of at least one fatty-chain allyl ether of formula (IV), and from 0% to 1% by weight of at least one crosslinking agent which may be a well-known copolymerizable unsaturated polyethylenic monomer, for instance diallyl phthalate, allyl (meth)acrylate, divinylbenzene, (poly)ethylene glycol dimethacrylate, and methylenebisacrylamide.

Among the latter polymers, those according to certain embodiments include crosslinked terpolymers of methacrylic acid, of ethyl acrylate and of polyethylene glycol (10 EO) stearyl ether alcohol (Steareth-10), such as those sold by the company Allied Colloids under the names SALCARE® SC 80 and SALCARE® SC 90, which are aqueous 30% emulsions of a crosslinked terpolymer of methacrylic acid, of ethyl acrylate, and of steareth-10 allyl ether, each unit comprising 40%, 50%, and 10%, respectively.

(II) anionic associative polymers comprising at least one unsaturated olefinic carboxylic acid hydrophilic unit, and at least one unsaturated carboxylic acid (C$_{10}$-C$_{30}$)alkyl ester hydrophobic unit.

These polymers may be chosen from those in which the unsaturated olefinic carboxylic acid hydrophilic unit corresponds to the monomer of formula (V) below:

$$H_2C=\underset{R16}{\overset{}{C}}-\underset{O}{\overset{\|}{C}}-OH \quad (V)$$

in which R16 is chosen from a hydrogen atom, CH$_3$, and C$_2$H$_5$, that is to say acrylic acid, methacrylic acid, and ethacrylic acid units, and in which the unsaturated carboxylic acid ($C_{10}$-$C_{30}$)alkyl ester hydrophobic unit corresponds to the monomer of formula (VI) below:

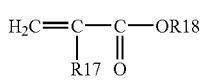  (VI)

in which

R17 is chosen from a hydrogen atom, $CH_3$, and $C_2H_5$, that is to say acrylate, methacrylate, and ethacrylate units, for example hydrogen, i.e., acrylate units, and $CH_3$, i.e., methacrylate units; and R18 is a $C_{10}$-$C_{30}$, such as a $C_{12}$-$C_{22}$ alkyl radical.

($C_{10}$-$C_{30}$) alkyl esters of unsaturated carboxylic acids according to certain embodiments may include, for example, lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate, and dodecyl methacrylate.

Anionic polymers of this type are described and prepared, for example, according to U.S. Pat. Nos. 3,915,921 and 4,509,949.

Among the anionic associative polymers of this type, those that may be mentioned include polymers formed from a monomer mixture comprising:

(i) at least one acrylic acid;

(ii) at least one ester of formula (VI) described above in which R17 is chosen from a hydrogen atom and $CH_3$, and R18 is chosen from alkyl radicals having from 12 to 22 carbon atoms;

(iii) and at least one crosslinking agent, which may be a well-known copolymerizable polyethylenic unsaturated monomer, for instance diallyl phthalate, allyl (meth)acrylate, divinylbenzene, (poly)ethylene glycol dimethacrylate, and methylenebisacrylamide.

Among fatty-chain anionic associative polymers of this type, those that may be mentioned include those comprising from 60% to 95% by weight of acrylic acid as the hydrophilic unit, from 4% to 40% by weight of $C_{10}$-$C_{30}$ alkyl acrylate as the hydrophobic unit, and from 0% to 6% by weight of crosslinking polymerizable monomer, or alternatively those comprising from 96% to 98% by weight of acrylic acid as the hydrophilic unit, from 1% to 4% by weight of $C_{10}$-$C_{30}$ alkyl acrylate as the hydrophobic unit, and from 0.1% to 0.6% by weight of crosslinking polymerizable monomer such as those described above.

Among the said above polymers, those that may be mentioned, by way of non-limiting example, are the products sold by the company Goodrich under the trade names PEMULEN® TR1, PEMULEN® TR2, and CARBOPOL® 1382, for example PEMULEN® TR1, and the product sold by the company SEPPIC under the name COATEX SX.

(III) maleic anhydride/$C_{30}$-$C_{38}$ α-olefin/alkyl maleate terpolymers, such as the product comprising maleic anhydride/$C_{30}$-$C_{38}$ α-olefin/isopropyl maleate copolymer sold under the name Performa V 1608 by the company Newphase Technologies.

(IV) acrylic terpolymers comprising:
  (a) 20% to 70% by weight of a carboxylic acid containing α,β-monoethylenic unsaturation,
  (b) 20% to 80% by weight of a non-surfactant monomer containing α,β-monoethylenic unsaturation and being other than (a),
  (c) 0.5% to 60% by weight of a non-ionic monourethane which is the product of reaction of a monohydric surfactant with a monoisocyanate containing monoethylenic unsaturation, such as those described in patent application EP A 0 173 109, for example the terpolymer described in Example 3, namely a methacrylic acid/methyl acrylate/ethoxylated (40 EO) behenyl dimethyl-meta-isopropenylbenzylisocyanate terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

These compounds may also comprise as monomer an ester of a carboxylic acid containing α,β-monoethylenic unsaturation and of a $C_1$-$C_4$ alcohol.

An example of a compound of this type which may be mentioned is ACULYN® 22 sold by the company Rohm & Haas, which is a methacrylic acid/ethyl acrylate/stearyl methacrylate oxyalkylenated terpolymer.

The non-ionic fatty-chain associative polymers used in accordance with the present disclosure include those chosen from:

(1) celluloses modified with at least one group comprising at least one fatty chain. Examples that may be mentioned include:
  hydroxyethylcelluloses modified with at least one group comprising at least one fatty chain, such as alkyl, arylalkyl, alkylaryl groups, and mixtures thereof, and in which the alkyl groups may be $C_8$-$C_{22}$, for instance the product NATROSOL® Plus Grade 330 CS, comprising $C_{16}$ alkyls and sold by the company Aqualon, or the product BERMOCOLL® EHM 100 sold by the company Berol Nobel,
  celluloses modified with alkylphenyl polyalkylene glycol ether groups, such as the product Amercell Polymer HM-1500, comprising nonylphenyl polyethylene glycol (15) ether and sold by the company Amerchol.

(2) hydroxypropylguars modified with groups comprising at least one fatty chain, such as the product Esaflor HM 22, comprising $C_{22}$ alkyl chains and sold by the company Lamberti, and the products RE210-18, comprising $C_{14}$ alkyl chains, and RE205-1, comprising $C_{20}$ alkyl chain, sold by the company Rhône-Poulenc.

(3) copolymers of vinylpyrrolidone and of fatty-chain hydrophobic monomers. Examples that may be mentioned include:
  the products Antaron V216 and Ganex, comprising vinylpyrrolidone/hexadecene copolymer and sold by the company I.S.P.
  the products Antaron V220 and Ganex V220, comprising vinylpyrrolidone/eicosene copolymer and sold by the company I.S.P.

(4) copolymers of $C_1$-$C_6$ alkyl methacrylates and $C_1$-$C_6$ alkyl acrylates, and of amphiphilic monomers comprising at least one fatty chain, such as, for example, the oxyethylenated methyl acrylate/stearyl acrylate copolymer sold by the company Goldschmidt under the name ANTIL® 208.

(5) copolymers of hydrophilic methacrylates and hydrophilic acrylates and of hydrophobic monomers comprising at least one fatty chain, such as, for example, polyethylene glycol methacrylate/lauryl methacrylate copolymer.

(6) polyurethane polyethers comprising in their chain both hydrophilic blocks usually of polyoxyethylenated nature and hydrophobic blocks which may be aliphatic sequences, cycloaliphatic sequences, and aromatic sequences.

(7) polymers with an aminoplast ether skeleton comprising at least one fatty chain, such as the PURE THIX® compounds sold by the company Sud-Chemie.

For example, the polyurethane polyethers may comprise at least two hydrocarbon-based lipophilic chains having from 8 to 30 carbon atoms, separated by a hydrophilic block, the hydrocarbon-based chains possibly being pendent chains or chains at the end of the hydrophilic block. It is possible for at least one pendent chain to be included. In addition, the polymer may comprise a hydrocarbon-based chain at one end or at both ends of a hydrophilic block.

The polyurethane polyethers may be multiblock, for example in triblock form. Hydrophobic blocks may be at each end of the chain, for example triblock copolymers with a hydrophilic central block, or distributed both at the ends and in the chain, for example, multiblock copolymers. These same polymers may also be graft polymers or starburst polymers.

The non-ionic fatty-chain polyurethane polyethers may be triblock copolymers in which the hydrophilic block is a polyoxyethylenated chain comprising from 50 to 1,000 oxyethylene groups. The non-ionic polyurethane polyethers may comprise a urethane linkage between the hydrophilic blocks, as the name indicates.

Also included among the non-ionic fatty-chain polyurethane polyethers are those in which the hydrophilic blocks are linked to the lipophilic blocks via other chemical bonds.

As examples of non-ionic fatty-chain polyurethane polyethers that may be used according to certain embodiments, mention may be made of RHEOLATE® 205 comprising a urea functional group, sold by the company Rheox, or the RHEOLATES® 208, 204, and 212, and also ACRYSOL® RM 184, ACULYN® 46, and ACULYN® 44 from the company Rohm & Haas. ACULYN® 46 is a polycondensate of polyethylene glycol comprising 150 or 180 mol of ethylene oxide, of stearyl alcohol, and of methylenebis(4-cyclohexyl isocyanate) (SMDI), at 15% by weight in a matrix of 4% maltodextrin and 81% water. ACULYN® 44 is a polycondensate of polyethylene glycol comprising 150 or 180 mol of ethylene oxide, of decyl alcohol, and of methylenebis(4-cyclohexylisocyanate) (SMDI), at 35% by weight in a mixture of 39% propylene glycol and 26% water.

Mention may also be made of the product ELFACOS® T210, comprising a $C_{12-14}$ alkyl chain, and the product ELFACOS® T212, comprising a $C_{18}$ alkyl chain, from Akzo.

The product DW 1206B from Rohm & Haas comprising a $C_{20}$ alkyl chain and a urethane linkage, sold at a solids content of 20% in water, may also be used.

It is also possible to use solutions or dispersions of these polymers, especially in water or in aqueous alcoholic medium. Examples of such polymers that may be mentioned are RHEOLATE® e 255, RHEOLATE® 278, and RHEOLATE® 244 sold by the company Rheox. The products DW 1206F and DW 1206J sold by the company Rohm & Haas may also be used. The polyurethane polyethers that may be used according to certain embodiments include those described in the article by G. Fonnum, J. Bakke and Fk. Hansen—Colloid Polym. Sci 271, 380.389 (1993).

The cationic fatty chain associative polymers as disclosed herein may be chosen from quaternized cellulose derivatives, polyacrylates comprising non-cyclic amine side groups, cationic polyurethanes, cationic polyvinyllactams, and the acrylic terpolymer whose constitution is given below.

The quaternized cellulose derivatives may be, for example, quaternized celluloses modified with at least one group comprising at least one fatty chain, such as alkyl, arylalkyl, and alkylaryl groups having at least 8 carbon atoms, and mixtures thereof, quaternized hydroxyethylcelluloses modified with groups comprising at least one fatty chain, such as alkyl, arylalkyl, and alkylaryl groups having at least 8 carbon atoms, and mixtures thereof.

The alkyl radicals borne by the above quaternized celluloses and hydroxyethylcelluloses may have from 8 to 30 carbon atoms. The aryl radicals may be chosen from phenyl, benzyl, naphthyl, and anthryl groups.

Examples of alkylhydroxyethylcelluloses quaternized with $C_8$-$C_{30}$ fatty chains that may be used include quaternized hydroxyethylcelluloses modified with at least one of $C_{12}$ and $C_{18}$ alkyl groups, such as the products QUATRISOFT LM 200, QUATRISOFT LM-X 529-18-A, QUATRISOFT LM-X 529-18B, which comprises a $C_{12}$ alkyl, and QUATRISOFT LM-X 529-8, which comprises a $C_{18}$ alkyl, which are sold by the company Amerchol, and the products Crodacel QM, Crodacel QL, comprising a $C_{12}$ alkyl, and Crodacel QS, comprising a $C_{18}$ alkyl, which are sold by the company Croda.

The polyacrylates comprising amine side groups, quaternized or non-quaternized, may possess, for example, steareth 20 hydrophobic groups, such as polyoxyethylenated (20) stearyl alcohol.

Examples that may be mentioned of polyacrylates comprising amine side chains include the polymers 8781-121B and 9492-103 provided by the company National Starch.

The cationic associative polyurethanes disclosed herein may be chosen from cationic associative amphiphilic polyurethanes, which may be water-soluble or water-dispersible.

As used herein, the term "water-soluble" or "soluble in water" in relation to the associative polyurethanes signifies that these polymers have a solubility in water at ambient temperature of at least 1% by weight; that is to say that, up to this concentration, no precipitate can be detected by the naked eye and the solution is clear and homogeneous.

As used herein, polyurethanes which are "water-dispersible" or "dispersible in water" are polymers which, when suspended in water, spontaneously form droplets having an average size, as measured by light scattering on a Coulter-type apparatus, ranging from 5 nm to 600 nm, such as from 5 nm to 500 nm.

The family of cationic amphiphilic polyurethanes disclosed herein has been described in French patent application No. 0 009 609. It may be represented by the general formula (Ia) below:

$$R19\text{-}X\text{—}(P)_n\text{-}[L\text{-}(Y)_m]_r\text{-}L'\text{-}(P')_p\text{—}X'\text{—}R20 \qquad (Ia)$$

in which:

R19 and R20, which may be identical or different, are chosen from hydrophobic groups and a hydrogen atom;

X and X', which may be identical or different, are chosen from groups comprising at least one amine function optionally bearing at least one hydrophobic group, and groups L";

L, L', and L", which may be identical or different, are chosen from groups derived from diisocyanate;

P and P', which may be identical or different, are chosen from groups comprising at least one amine function optionally bearing at least one hydrophobic group;

Y is chosen from hydrophilic groups;

r is an integer ranging from 1 to 100, such as from 1 to 50 or from 1 to 25; and n, m, and p, which may be identical or different, range from 0 to 1,000;

wherein the molecule comprises at least one protonated or quaternized amine function and at least one hydrophobic group.

In one embodiment of the polyurethanes disclosed herein, the only hydrophobic groups are the groups R19 and R20 at the chain ends.

One suitable family of cationic amphiphilic polyurethanes is the one corresponding to formula (Ia) described above and in which:

R19 and R20 are each independently chosen from hydrophobic groups;

X and X' each represent a group L";

n and p range from 1 to 1000; and

L, L', L", P, P', Y, r, and m have the meanings given above.

In another embodiment, the family of cationic amphiphilic polyurethanes is the one corresponding to formula (Ia) above in which:

R19 and R20 are each independently chosen from hydrophobic groups, X and X' each represent a group L", n and p are 0, and L, L', L", Y, r, and m have the meaning given above.

The fact that n and p are 0 means that these polymers do not comprise units derived from a monomer comprising an amine function, incorporated into the polymer during the polycondensation. The protonated amine functions of these polyurethanes may result from the hydrolysis of excess isocyanate functions, at the chain end, followed by alkylation of the primary amine functions formed with alkylating agents comprising a hydrophobic group, i.e., compounds of the type R19Q or R20Q, in which R19 and R20 are as defined above and Q denotes a leaving group such as halides and sulphates.

In yet another embodiment, the family of cationic amphiphilic polyurethanes is the one corresponding to formula (Ia) above in which:

R19 and R20 are each independently chosen from hydrophobic groups;

X and X' are each independently chosen from a group comprising at least one quaternary amine;

n and p are 0; and

L, L', Y, r, and m have the meanings given above.

The number-average molecular mass of the cationic associative polyurethanes may range from 400 to 500,000, such as from 1,000 to 400,000 or from 1,000 to 300,000.

As used herein, the expression "hydrophobic group" means a radical or polymer comprising a saturated or unsaturated, linear or branched hydrocarbon-based chain, which may comprise at least one heteroatom such as P, O, N, and S, or a radical comprising at least one of perfluoro and silicone chains. When the hydrophobic group is chosen from hydrocarbon-based radicals, it may comprise at least 10 carbon atoms, such as 10 to 30 carbon atoms, for example 12 to 30 carbon atoms or 18 to 30 carbon atoms. The hydrocarbon-based group may be derived from a monofunctional compound.

By way of example, the hydrophobic group may be derived from a fatty alcohol such as stearyl alcohol, dodecyl alcohol, and decyl alcohol. It may also denote a hydrocarbon-based polymer such as, for example, polybutadiene.

When X and/or X' are chosen from a group comprising at least one tertiary or quaternary amine, X and/or X' may represent one of the following formulae:

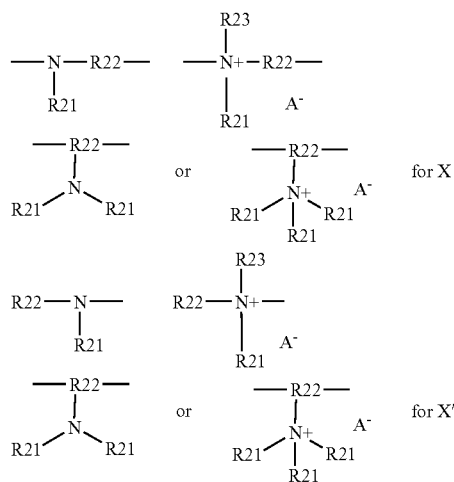

in which:

R22 is chosen from linear and branched alkylene radicals having from 1 to 20 carbon atoms, optionally comprising at least one of a saturated or unsaturated ring, and an arylene radical, at least one of the carbon atoms optionally being replaced with at least one heteroatom chosen from N, S, O, and P;

R21 and R23, which may be identical or different, are chosen from linear and branched $C_1$-$C_{30}$ alkyls and alkenyl radicals and aryl radicals, at least one of the carbon atoms optionally being replaced with at least one heteroatom chosen from N, S, O, and P; and $A^-$ is a physiologically acceptable counter-ion.

According to another aspect, the groups L, L', and L" represent a group of formula:

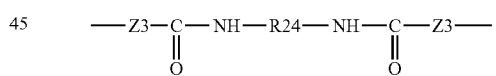

in which:

Z3 is chosen from —O—, —S—, and —NH— groups; and

R24 is chosen from linear and branched alkylenes having from 1 to 20 carbon atoms, optionally comprising at least one of saturated and unsaturated rings and arylene radicals, at least one of the carbon atoms optionally being replaced with at least one heteroatom chosen from N, S, O, and P.

The groups P and P' comprising an amine function may be chosen from at least one of the following formulae:

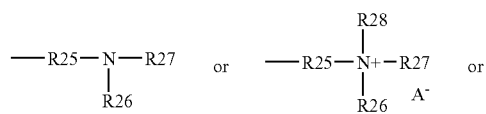

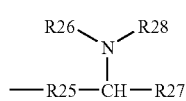 or 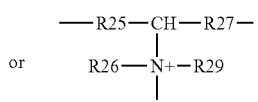 or

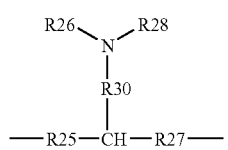 or 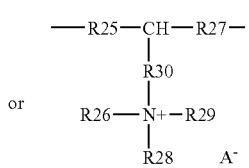

in which:

R25 and R27 have the same meanings as R22 defined above;

R26, R28, and R29 have the same meanings as R21 and R23 defined above;

R30 is chosen from linear and branched, saturated and unsaturated alkylene groups, optionally comprising at least one heteroatom chosen from N, O, S, and P; and A$^-$ is a physiologically acceptable counter-ion.

As regards the meaning of Y, the term "hydrophilic group" means a polymeric or non-polymeric water-soluble group.

By way of example, when Y is not a polymer, mention may be made of ethylene glycol, diethylene glycol, and propylene glycol.

When Y is a hydrophilic polymer, in accordance with one embodiment, mention may be made, for example, of polyethers, sulphonated polyesters, sulphonated polyamides, and mixtures of these polymers. The hydrophilic compound may be a polyether such as poly(ethylene oxide) and poly(propylene oxide).

The cationic associative polyurethanes of formula (Ia) according to the present disclosure may be formed from diisocyanates and from various compounds with functional groups comprising labile hydrogen. The functional groups comprising labile hydrogen may be chosen from alcohol, primary amines, secondary amines, and thiol functions giving, after reaction with the diisocyanate functions, polyurethanes, polyureas, and polythioureas, respectively. The term "polyurethanes" as used herein encompasses these three types of polymer, namely polyurethanes per se, polyureas, and polythioureas, as well as copolymers thereof.

A first type of compound involved in the preparation of the polyurethane of formula (Ia) may be a compound comprising at least one unit comprising an amine function. This compound may be multifunctional, or for example may be difunctional, that is to say that, according to one embodiment, this compound comprises two labile hydrogen atoms derived, for example, from at least one of hydroxyl, primary amine, secondary amine, and thiol functions. A mixture of multifunctional and difunctional compounds in which the percentage of multifunctional compounds is low may also be used.

As mentioned above, this compound may comprise more than one unit comprising an amine function. In this case, it is a polymer having a repetition of the unit comprising an amine function.

Compounds of this type may be chosen from the following formulae:

HZ3-(P)$_n$-ZH and

HZ3-(P')$_p$-ZH in which Z3, P, P', n and p are as defined above.

Examples of compounds comprising an amine function that may be mentioned include N-methyldiethanolamine, N-tert-butyldiethanolamine, and N-sulphoethyldiethanolamine.

The second compound involved in the preparation of the polyurethane of formula (Ia) may be a diisocyanate corresponding to the formula:

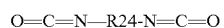

in which R24 is as defined above.

By way of example, mention may be made of methylenediphenyl diisocyanate, methylenecyclohexane diisocyanate, isophorone diisocyanate, toluene diisocyanate, naphthalene diisocyanate, butane diisocyanate, and hexane diisocyanate.

A third compound involved in the preparation of the polyurethane of formula (Ia) may be a hydrophobic compound intended to form the terminal hydrophobic groups of the polymer of formula (Ia).

This third compound may comprise a hydrophobic group and a functional group comprising labile hydrogen, for example hydroxyl, primary amine, secondary amine, and thiol functions.

By way of example, this third compound may be a fatty alcohol such as for example, stearyl alcohol, dodecyl alcohol, and decyl alcohol. When this compound comprises a polymeric chain, it may be, for example, α-hydroxylated hydrogenated polybutadiene.

The hydrophobic group of the polyurethane of formula (Ia) may also result from the quaternization reaction of the tertiary amine of the compound comprising at least one tertiary amine unit. Thus, the hydrophobic group may be introduced via the quaternizing agent. This quaternizing agent may be a compound of the type R19Q or R20Q, in which R19 and R20 are as defined above and Q is chosen from leaving groups such as, for example, halides and sulphates.

The cationic associative polyurethane may also comprise a hydrophilic block. This block may be provided by a fourth type of compound involved in the preparation of the polymer. This fourth compound may be multifunctional. In certain embodiments, the fourth compound is difunctional. It is also possible to have a mixture in which the percentage of multifunctional compound is low.

The functional groups comprising labile hydrogen may be chosen from alcohol, primary amine, secondary amine, and thiol functions. This fourth compound may be a polymer terminated at the chain ends with one of these functional groups comprising labile hydrogen.

By way of example, when it is not a polymer, it may be chosen from, by way of non-limiting example, ethylene glycol, diethylene glycol, and propylene glycol.

When it is a hydrophilic polymer, mention may be made, for example, of polyethers, sulphonated polyesters, sulphonated polyamides, and mixtures of these polymers. The hydrophilic compound may be a polyether, such as poly(ethylene oxide) and poly(propylene oxide).

The hydrophilic group termed Y in formula (Ia) is optional. Specifically, the units comprising a quaternary amine or protonated function may suffice to provide the solubility or water-dispersibility required for this type of polymer in an aqueous solution.

Although the presence of a hydrophilic group Y is optional, cationic associative polyurethanes comprising such a group may be mentioned.

The said cationic associative polyurethanes are water-soluble or water-dispersible.

The cationic poly(vinyllactam) polymers according to certain embodiments comprise:

a) at least one monomer chosen from vinyllactams and alkylvinyllactams;

b) at least one monomer chosen from structures (Ib) and (IIb) below:

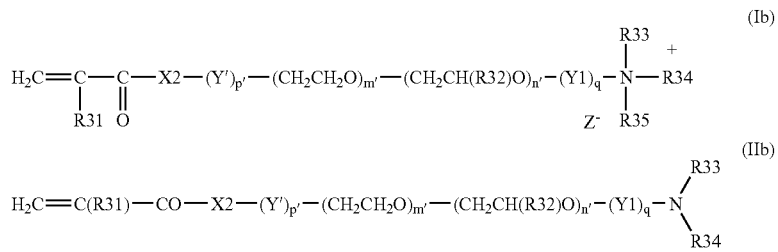

in which:

X2 is chosen from an oxygen atom and NR36;

R31 and R36, which may be identical or different, are chosen from a hydrogen atom and linear and branched $C_1$-$C_5$ alkyl radicals;

R32 is chosen from linear and branched $C_1$-$C_4$ alkyl radicals;

R33, R34, and R35, which may be identical or different, are chosen from a hydrogen atom, linear and branched $C_1$-$C_{30}$ alkyl radicals, and radicals of formula (IIIb):

$$-(Y2)_r\text{-}(CH_2-CH(R37\text{-}O)_x-R38 \quad (IIIb)$$

Y', Y1, and Y2, which may be identical or different, are chosen from linear and branched $C_2$-$C_{16}$ alkylene radicals;

R37 is chosen from a hydrogen atom, linear and branched $C_1$-$C_4$ alkyl radicals, and linear and branched $C_1$-$C_4$ hydroxyalkyl radicals;

R38 is chosen from a hydrogen atom and linear and branched $C_1$-$C_{30}$ alkyl radicals;

p', q, and r', which may be identical or different, are chosen from the values zero and 1;

m' and n', which may be identical or different, are chosen from integers ranging from 0 to 100;

x is chosen from integers ranging from 1 to 100; and

Z is chosen from organic and mineral acid anions, with the proviso that:

at least one of the substituents R33, R34, R35, and R38 is chosen from linear and branched $C_9$-$C_{30}$ alkyl radicals, if m' or n' is other than zero, then q is equal to 1, if m' or n' are equal to zero, then p' or q is equal to 0.

The cationic poly(vinyllactam) polymers disclosed herein may be crosslinked or non-crosslinked, and may also be block polymers.

The counter-ion Z⁻ of the monomers of formula (Ib) may be chosen from halide ions, phosphate ions, methosulphate ions, and tosylate ions.

For example, R33, R34, and R35, which may be identical or different, may be chosen from a hydrogen atom and linear and branched $C_1$-$C_{30}$ alkyl radicals.

In one embodiment, the monomer b) is a monomer of formula (Ib) for which m' and n' are equal to zero.

The vinyllactam or alkylvinyllactam monomer may be a compound of structure (IVb):

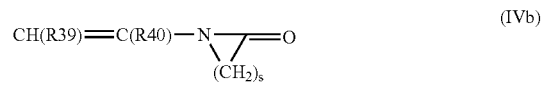

in which:

s is an integer ranging from 3 to 6;

R39 is chosen from a hydrogen atom and $C_1$-$C_5$ alkyl radicals; and

R40 is chosen from a hydrogen atom and $C_1$-$C_5$ alkyl radicals;

with the proviso that at least one of the radicals R39 and R40 is hydrogen.

For example, the monomer (IVb) is vinylpyrrolidone.

The cationic poly(vinyllactam) polymers disclosed herein may also comprise at least one additional monomer, which may be cationic or non-ionic.

In certain embodiments, mention may be made of the following terpolymers comprising at least:

a)—a monomer of formula (IVb);

b)—a monomer of formula (Ib) in which p' is 1; q is 0; R33 and R34, which may be identical or different, are chosen from a hydrogen atom and $C_1$-$C_5$ alkyl radicals; and R35 is chosen from $C_9$-$C_{24}$ alkyl radicals; and c)—a monomer of formula (IIb) in which R33 and R34, which may be identical or different, are chosen from a hydrogen atom and $C_1$-$C_5$ alkyl radicals.

For example, terpolymers comprising, on a weight basis, 40% to 95% of monomer (a), 0.1% to 55% of monomer (c), and 0.25% to 50% of monomer (b) may be used.

Such polymers are described in patent application WO 00/68282, the content of which is incorporated by reference herein.

Cationic poly(vinyllactam) polymers according to certain embodiments that may be used include: vinylpyrrolidone/dimethylaminopropylmethacrylamide/-dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, and vinylpyrrolidone/dimethylaminopropylmethacrylamide/lauryldimethylmethacrylamidopropylammonium tosylate and chloride terpolymers.

The weight-average molecular mass of the cationic poly(vinyllactam) polymers disclosed herein may range from 500 to 20,000,000, such as from 200,000 to 2,000,000 or from 400,000 to 800,000.

Among the cationic amphiphilic polymers disclosed herein, mention may also be made of acrylic terpolymers as described in patent application EP 1 090 623 and which may comprise:

from 5% to 80% by weight, such as from 15% to 70% by weight or from 40% to 70% by weight of an acrylate monomer (a) chosen from $C_1$-$C_6$ alkyl acrylates and $C_1$-$C_6$ alkyl methacrylates;

from 5% to 80% by weight, such as from 10% to 70% by weight or from 20% to 60% by weight, of a monomer (b) chosen from heterocyclic vinyl compounds comprising at least one of nitrogen and sulphur atoms, (meth)acrylamide, mono- and di($C_1$-$C_4$)alkylamino($C_1$-$C_4$)alkyl (meth)acrylate, and mono- and di($C_1$-$C_4$)alkylamino($C_1$-$C_4$)alkyl(meth)acrylamide;

from 0.1% to 30% by weight, such as from 0.1% to 10% by weight, of a monomer (c) chosen from:
  (i) at least one urethane produced by reaction between a monoethylenic unsaturated isocyanate and a non-ionic surfactant with a $C_{1-4}$ alkoxy end;
  (ii) at least one block copolymer of 1,2-butylene oxide and of 1,2-ethylene oxide;
  (iii) at least one copolymerizable ethylenic unsaturated surfactant monomer obtained by condensation of a non-ionic surfactant with an α,β-ethylenic unsaturated carboxylic acid or its anhydride;
  (iv) at least one surfactant monomer chosen from the products of a reaction such as a urea of a monoethylenic unsaturated monoisocyanate with a non-ionic surfactant comprising at least one amine function;
  (v) at least one (meth)allyl ether of formula $CH_2$=C(R41) $CH_2O(A2)_{m''}(B1)_{n''}A2_{p''}(R42)$ in which R41 is chosen from a hydrogen atom and methyl groups; A2 is chosen from propylenoxy and butylenoxy groups; B1 denotes ethylenoxy; n" is chosen from an integer ranging from 0 to 200, such as less than 100; m" and p" are chosen from zero and integers less than n"; and R42 is chosen from hydrophobic groups having at least 8 carbon atoms, for example $C_8$-$C_{30}$; and
  (vi) at least one non-ionic urethane monomer produced by reaction of a monohydric non-ionic surfactant with a monoethylenic unsaturated isocyanate;

wherein the weight percentages of monomer is based on the total weight of the monomers comprising the terpolymer.

Acrylate monomers (a) that may be used comprise, for example, $C_2$-$C_6$ alkyl acrylates. Mention may be made of the use of ethyl acrylate as an acrylate monomer (a).

Examples of monomers (b) which may be mentioned include N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide, and N,N-diethylaminopropylmethacrylamide. N,N-dimethylaminoethyl methacrylate may, for example, be used.

The monomers (c) may be the copolymerizable ethylenic unsaturated surfactant monomers obtained by condensing a non-ionic surfactant with an α,β-ethylenic unsaturated carboxylic acid or its anhydride, such as $C_3$-$C_4$ mono- or dicarboxylic acids or their anhydrides, for example acrylic acid, methacrylic acid, crotonic acid, maleic acid, maleic anhydride, itaconic acid, and itaconic anhydride.

The monomers (c) that may be used according to certain embodiments correspond to the copolymerizable ethylenic unsaturated surfactant monomers obtained by condensing a non-ionic surfactant with itaconic acid. Among the non-ionic surfactants which may be mentioned are $C_{10}$-$C_{30}$ fatty alcohols alkoxylated with 2 to 100 mol, such as from 5 to 50 mol of an alkylene oxide, such as, for example, polyethylene glycol ethers of $C_{10}$-$C_{30}$ fatty alcohols, for example the polyethylene glycol ethers of cetyl alcohol which are called CETETH in the CTFA dictionary, 7th edition, 1997.

Acrylic terpolymers may thus be chosen from acrylic terpolymers comprising acrylates, amino(meth)acrylates, and $C_{10}$-$C_{30}$ alkyl itaconate, polyoxyethylenated with 20 mol of ethylene oxide.

Conventional methods for preparing these acrylic terpolymers are known to those skilled in the art. Such methods include solution polymerization, precipitation polymerization, and emulsion polymerization. Terpolymers in accordance with certain embodiments and methods for preparing them are described for example in patent applications EP A 0 824 914 and EP A 0 825 200.

Among these terpolymers, mention may be made of the use the "Structure® Plus" polymer sold by the company National Starch, which comprises acrylates, amino (meth) acrylates, and $C_{10}$-$C_{30}$ alkyl itaconate, polyoxyethylenated with 20 mol of ethylene oxide, in the form of an aqueous dispersion comprising 20% active material.

In addition to these monomers, the terpolymers can comprise other monomers which allow the said terpolymers to be crosslinked. These monomers may be used in relatively low proportions, of up to 2% by weight relative to the total weight of the monomers used to prepare the terpolymers. Such crosslinking monomers may be chosen from aromatic monomers having several vinyl substituents, alicyclic monomers having several vinyl substituents, bifunctional esters of phthalic acid, bifunctional esters of methacrylic acid, multifunctional esters of acrylic acid, N-methylenebisacrylamide, and aliphatic monomers having several vinyl substituents such as dienes, trienes, and tetraenes.

Crosslinking monomers may be, for example, divinylbenzenes, trivinylbenzenes, 1,2,4-trivinylcyclohexene, 1,5-hexadiene, 1,5,9-decatriene, 1,9-decadiene, 1,5-heptadiene, diallyl phthalates, ethylene glycol dimethacrylate, polyethylene glycol dimethacrylates, penta- and tetraacrylates, triallyl pentaerythritols, octaallyl sucroses, cycloparaffins, cycloolefins, and N-methylenebisacrylamide.

The at least one associative polymer disclosed herein may also be chosen from amphoteric associative polymers.

As used herein, the term "amphoteric polymers" generally denotes polymers which comprise units K and M randomly distributed in the polymer chain, where K denotes a unit derived from a monomer comprising at least one basic nitrogen atom, and M denotes a unit deriving from an acidic monomer comprising at least one of carboxylic and sulphonic groups, or K and M may denote groups deriving from at least one of zwitterionic carboxybetaine and sulphobetaine monomers;

K and M may also denote a cationic polymer chain comprising at least one of primary, secondary, tertiary, and quaternary amine groups, in which at least one of the amine groups bears a carboxylic or sulphonic group linked via a hydrocarbon-based radical, or K and M may form part of a chain of a polymer comprising an α,β-dicarboxylic ethylene unit in which one of the carboxylic groups has been made to react with a polyamine comprising at least one of primary and secondary amine groups.

The amphoteric polymers used according to certain embodiments may further comprise at least one fatty chain having 8 to 30 carbon atoms, and may be chosen, for example, from polymers derived from polyaspartic acid and comprising at least one fatty chain having 8 to 30 carbon atoms, such as those:

described and prepared in patent application EP 0 767 191, the content of which is incorporated by reference herein. Such polymers may be prepared in a conventional manner by reacting polysuccinimide (PSI) with fatty-chain ($C_8$-$C_{24}$) amines in a solvent medium in the presence or absence of a basic catalyst such as, for example, aliphatic tertiary amines, followed by amphoterization of the resultant product by reaction with a halogenated organic acid.

Among the $C_8$-$C_{24}$ fatty-chain amines which may be reacted with the PSI, mention may be made of octylamine, nonylamine, decylamine, dodecylamine, tetradecylamine, hexadecylamine, octadecylamine, octadecenylamine, eicosyldecylamine, octynylamine, decenylamine, dodecenylamine, tetradecenylamine, hexadecenylamine, octadecenylamine, and eicosenylamine.

Examples of such polymers are prepared by reacting PSI with n-laurylamine or with n-stearylamine in the presence of N,N-dimethyl-1,3-propanediamine as basic catalyst, followed by amphoterization of the resultant product by reaction with potassium monochloroacetate. These polymers are prepared with greater details on pages 13 to 20 (lines 1-4) and in Examples 1 to 5 on pages 28 to 34 (lines 14) of the said patent application EP 0 767 191.

described and prepared in patent application EP 0 884 344, the contents of which are incorporated by reference herein. Polymers of this kind may be prepared by reacting gaseous ammonia with a $C_8$-$C_{24}$ alkyl or alkenyl monomaleate in a solvent medium under reduced pressure at a temperature of 120-140° C. for from 4 to 6 hours.

The $C_8$-$C_{24}$ alkyl or alkenyl radicals may be chosen from linear and branched radicals such as decyl, dodecyl, tetradecyl, hexadecyl, octadecyl, and oleyl radicals.

Examples of such polymers include polymers comprising aspartic acid units and decyl aspartate units, polymers comprising aspartic acid units and dodecyl aspartate units, polymers comprising aspartic acid units and cetyl aspartate units, polymers comprising aspartic acid units and stearyl aspartate units, and polymers comprising aspartic acid units and n-decylaspartamide units, which are described, for example, in Examples 1 to 6 in the said patent application EP 0 884 344.

described and prepared in patent application EP 0 959 094, the contents of which are incorporated by reference herein. Polymers of this kind may be prepared by reacting, in a solvent medium, gaseous ammonia with maleic acid monoamide, polyoxyalkylenated and hydrophobically modified by a at least one of linear or branched $C_8$-$C_{30}$ alkyls and alkenyl chains, optionally in a mixture with at least one monoester of maleic acid.

An example of a polymer thus prepared is described in Example 2 on page 11 of the said patent application EP 0 959 094.

described and prepared in patent application EP 0 959 090, the contents of which are incorporated by reference herein. Hydrophobically modified polymers of this kind of high molecular weight may be obtained from derivatives of maleic acid and gaseous ammonia and from difunctional or polyfunctional amines and alcohols.

Examples of copolymers comprising aspartic acid units and cetyl aspartate units and comprising aspartic acid units and cetyl aspartate units are given, respectively, in Examples 3 and 5 of the said patent application EP 0 959 090.

described and prepared in patent application EP 0 959 091, the contents of which are incorporated by reference herein. Hydrophobically modified polymers of this kind may be prepared from at least one of maleic acid monoester, maleic acid monoamide, and gaseous ammonia.

Examples of such copolymers are given in Examples 1, 2, 3, and 5 of the said patent application EP 0 959 091.

In accordance with the present disclosure, the amphoteric polymers comprising at least one fatty chain having 8 to 30 carbon atoms may be chosen from those comprising at least one non-cyclic cationic unit. For example, the amphoteric polymers may be prepared from or comprise from 1 to 20 mol % of monomer comprising a fatty chain, such as from 1.5 to 15 mol % or from 1.5 to 6 mol %, relative to the total number of moles of monomers.

The said fatty-chain amphoteric polymers of which mention may be made comprise, or are prepared by copolymerizing:

1) at least one monomer of formula (Va) or (Vb):

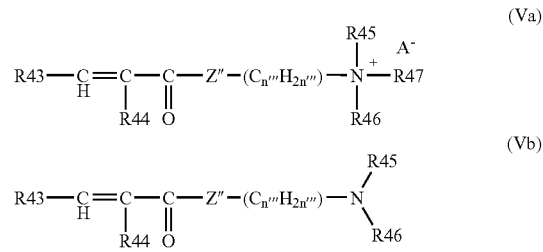

in which R43 and R44, which may be identical or different, are chosen from a hydrogen atom and methyl; R45, R46, and R47, which may be identical or different, are chosen from linear and branched alkyl radicals having from 1 to 30 carbon atoms;

Z″ is chosen from an NH group and an oxygen atom;

n‴ is an integer from 2 to 5; and

A⁻ is an anion derived from an acid chosen from organic and mineral acids, such as methosulphate anions and halides such as chloride and bromide;

2) at least one monomer of formula (VI)

in which R48 and R49, which may be identical or different, are chosen from a hydrogen atom and methyl; and 3) at least one monomer of formula (VII):

in which R48 and R49, which may be identical or different, are chosen from a hydrogen atom and methyl, X‴ is chosen from oxygen and nitrogen, and R50 is chosen from linear and branched alkyl radicals having from 1 to 30 carbon atoms; wherein at least one of the monomers of formula (Va), (Vb) and (VII) comprises at least one fatty chain.

The monomers of formulae (Va) and (Vb) disclosed herein may be chosen from:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, and dimethylaminopropylacrylamide, these monomers optionally being quaternized, for example with a $C_1$-$C_4$ alkyl halide or a $C_1$-$C_4$ dialkyl sulphate.

In according with the present disclosure, the monomer of formula (Va) may be chosen from acrylamidopropyltrimethylammonium chloride and methacrylamidopropyltrimethylammonium chloride.

The monomers of formula (VI) disclosed herein may be chosen from acrylic acid, methacrylic acid, crotonic acid, and 2-methylcrotonic acid. For example, the monomer of formula (VI) may be acrylic acid.

The monomers of formula (VII) disclosed herein may be chosen from $C_{12}$-$C_{22}$, such as $C_{16}$-$C_{18}$, alkyl acrylates and methacrylates.

The monomers comprising the fatty-chain amphoteric polymers disclosed herein may be already neutralized and/or quaternized.

The ratio of the number of cationic charges to anionic charges is, in certain embodiments, to about 1.

The fatty-chain amphoteric polymers disclosed herein may comprise from 1 mol % to 10 mol % of the monomer comprising a fatty chain, such as monomers of formula (Va), (Vb), and (VII), for example from 1.5 mol % to 6 mol %.

The weight-average molecular weights of the fatty-chain amphoteric polymers disclosed herein may range from 500 to 50,000,000, such as from 10,000 to 5,000,000.

The fatty-chain amphoteric polymers may also comprise other monomers such as non-ionic monomers, $C_1$-$C_4$ alkyl acrylates and methacrylates.

Fatty-chain amphoteric polymers disclosed here are described and prepared, for example, in patent application WO 98/44012.

Among the fatty-chain amphoteric polymers, the ones that may be mentioned are are acrylic acid/(meth)acrylamidopropyltrimethylammonium chloride/stearyl methacrylate terpolymers.

In the oxidation dyeing composition disclosed herein a fatty-chain cationic or non-ionic associative polymer may be used, For example, the at least one associative polymer is chosen from cationic polyurethanes.

The at least one associative polymer may be present in the composition in an amount ranging from 0.05% to 10%, such as from 0.1% to 5% by weight, relative to the total weight of the composition.

The ratio by weight of the amide of an alkanolamine and a $C_{14}$-$C_{30}$ acid to the at least one associative polymer may range from 0.5 to 40, such as from 1 to 20 or from 5 to 20.

The ratio by weight of the amide of an alkanolamine and a $C_{14}$-$C_{30}$ fatty acid to the at least one non-oxyethylenated fatty alcohol may range from 0.1 to 10, such as from 0.5 to 5.

The composition (A) and/or the composition (B) may further comprise, for example, at least one cationic or amphoteric substantive polymer different from the associative polymers disclosed herein.

As used herein, the term "cationic polymer" denotes any polymer comprising at least one of cationic groups and groups that may be ionized into cationic groups.

The cationic substantive polymers that may be used in accordance with certain embodiments may be chosen from all those already known per se as improving the cosmetic properties of the hair, such as those described in patent application EP A 337 354 and in French Patent Nos. FR 2 270 846, 2 383 660, 2 598 611, 2 470 596, and 2 519 863.

The cationic polymers of which mention may be made may be chosen from those comprising units comprising at least one of primary, secondary, tertiary, and quaternary amine groups, which may either form part of the main polymer chain or may be derived from a side substituent attached directly thereto.

The cationic polymers used generally have a number-average molecular mass ranging from 500 to $5 \times 10^6$, such as from $10^3$ to $3 \times 10^6$.

Among the cationic polymers those that may also be mentioned are polymers chosen from polyamine, polyamino amide, and polyquaternary ammonium polymers.

These are known products. They are described for example in French Patents Nos. 2 505 348 and 2 542 997. Among the said polymers, mention may be made of:

(1) homopolymers or copolymers derived from at least one of acrylic, methacrylic esters, and amides, comprising at least one of the units of formula (VIII), (IX), (X), and (XI) below:

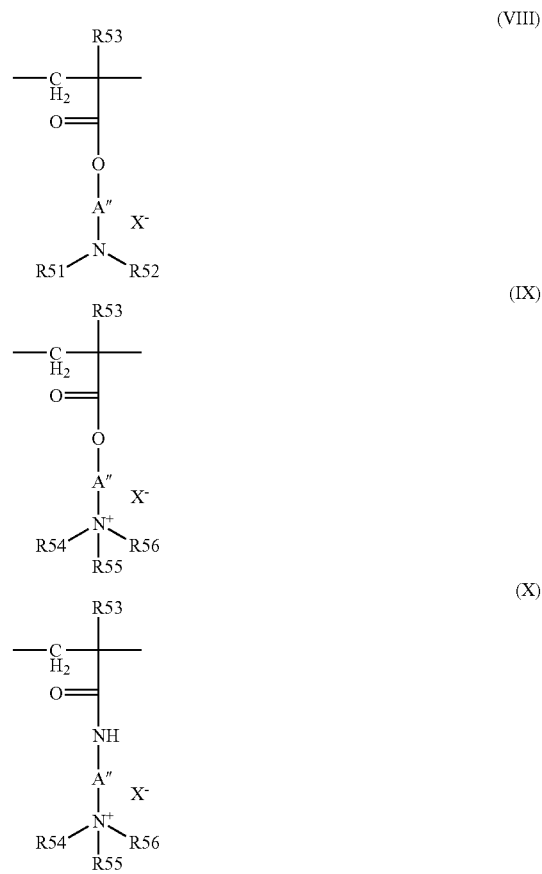

-continued

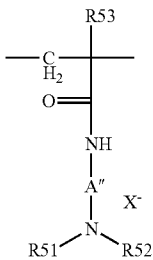

(XI)

in which:

R53, which may be identical or different, are chosen from a hydrogen atom and $CH_3$;

A″, which may be identical or different, is chosen from linear and branched alkyl groups having 1 to 6 carbon atoms, such as 2 or 3 carbon atoms, and hydroxyalkyl groups having 1 to 4 carbon atoms;

R54, R55, and R56, which may be identical or different, are chosen from alkyl groups having from 1 to 6 carbon atoms;

R51 and R52, which may be identical or different, are chosen from a hydrogen atom and alkyl groups having from 1 to 6 carbon atoms, for example methyl and ethyl groups;

X denotes an anion derived from an acid chosen from inorganic and organic acids, such as methosulphate anions and halides such as chloride and bromide.

The polymers of family (1) may also comprise at least one unit derived from comonomers which may be chosen from the family of acrylamides, methacrylamides, diacetone acrylamides, acrylamides, and methacrylamides substituted on the nitrogen with at least one of lower ($C_1$-$C_4$) alkyls, acrylic acids, methacrylic acids, and esters thereof, vinyllactams such as vinylpyrrolidone and vinylcaprolactam, and vinyl esters. Thus, among these polymers of family (1), mention may be made of:

copolymers of acrylamide and of dimethylaminoethyl methacrylate quaternized with dimethyl sulphate or with a dimethyl halide, such as the product sold under the name HERCOFLOC® by the company Hercules;

the copolymers of acrylamide and of methacryloyloxyethyltrimethylammonium chloride described, for example, in patent application EP A 080 976 and sold under the name Bina Quat P 100 by the company Ciba Geigy;

the copolymers of acrylamide and of methacryloyloxyethyltrimethylammonium methosulphate sold under the name RETEN® by the company Hercules;

quaternized or non-quaternized vinylpyrrolidone/dialkylaminoalkyl acrylate and methacrylate copolymers, such as the products sold under the name GAFQUAT® by the company ISP, such as, for example, GAFQUAT® 734 and GAFQUAT® 755, or alternatively the products known as Copolymer 845, 958, and 937. These polymers are described in detail in French Patent Nos. 2 077 143 and 2 393 573;

dimethylaminoethyl methacrylate/vinylcaprolactam/vinylpyrrolidone terpolymers, such as the product sold under the name GAFFIX® VC 713 by the company ISP;

vinylpyrrolidone/methacrylamidopropyldimethylamine copolymers sold for exmaple under the name STYLEZE® CC 10 by ISP; and quaternized vinylpyrrolidone/dimethylaminopropylmethacrylamide copolymers such as the product sold under the name GAFQUAT® HS 100 by the company ISP.

(2) The cellulose ether derivatives comprising quaternary ammonium groups, described in French patent 1 492 597, such as polymers sold under the names JR, such as JR 400, JR 125, and JR 30M and LR, such as LR 400 and LR 30M, sold by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers and cellulose derivatives grafted with a water-soluble monomer of quaternary ammonium, and described for example in U.S. Pat. No. 4,131,576, such as hydroxyalkylcelluloses, for instance hydroxymethyl-, hydroxyethyl-, and hydroxypropylcelluloses grafted, for example, with a salt chosen from methacryloylethyltrimethylammonium, methacrylamidopropyltrimethylammonium, and dimethyidiallylammonium salts The commercial products corresponding to this definition are for example the products sold under the names CELQUAT® L 200 and CELQUAT® H 100 by the company National Starch.

(4) The cationic polysaccharides described for example in U.S. Pat. Nos. 3,589,578 and 4,031,307, such as guar gums comprising cationic trialkylammonium groups. For example, guar gums modified with a salt, such as chloride, of 2,3-epoxypropyltrimethylammonium may be used.

Such products are sold under the trade names JAGUAR® C13 S, JAGUAR® C 15, JAGUAR® C 17, and JAGUAR® C162 by the company Meyhall.

(5) Polymers comprising racidals chosen from piperazinyl radicals, divalent alkylene radicals, and hydroxyalkylene radicals comprising straight or branched chains, optionally interrupted by at least one of oxygen, sulphur, and nitrogen atoms, and aromatic and heterocyclic rings, as well as the oxidation and/or quaternization products of these polymers. Such polymers are described, for example, in French Patent Nos. 2 162 025 and 2 280 361.

(6) Water-soluble polyamino amides prepared for example by polycondensation of an acidic compound with a polyamine. These polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative. The crosslinking agent may be used in proportions ranging from 0.025 to 0.35 mol per amine group of the polyamino amide. These polyamino amides can be alkylated or, if they comprise at least one tertiary amine functions, they can be quaternized. Such polymers are described, for example, in French Patent Nos. 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms, for example methyl, ethyl, and propyl radicals. Such polymers are described for example in French Patent No. 1 583 363.

Among these derivatives, mention may be made of the adipic acid/dimethylaminohydroxypropyl/diethylenetriamine polymers sold under the name "Cartaretine F, F4, and F8" by the company Sandoz.

(8) The polymers obtained by reaction of a polyalkylene polyamine comprising two primary amine groups and at least one secondary amine group with a dicarboxylic acid chosen from diglycolic acid and saturated aliphatic dicarboxylic acids having from 3 to 6 carbon atoms. The molar ratio between the polyalkylene polyamine and the dicarboxylic acid may range from 0.8:1 to 1.4:1; the polyamino amide resulting therefrom may be reacted with epichlorohydrin in a molar ratio of epichlorohydrin relative to the secondary amine group of the polyamino amide ranging from 0.5:1 to 1.8:1. Such polymers are described for example in U.S. Pat. Nos. 3,227,615 and 2,961,347.

Polymers of this type are sold under the name HERCOSETT® 57 by the company Hercules Inc. or alternatively under the name PD 170 or DELSETTE® 101 by the company Hercules in the case of the adipic acid/epoxypropyl/diethylenetriamine copolymer.

(9) Cyclopolymers of alkyldiallylamine or of dialkyldiallylammonium, such as the homopolymers or copolymers comprising, as the main constituent of the chain, units corresponding to formula (XII) or (XIII):

$$\begin{array}{c} \text{CR9}' \diagup^{(CH_2)k'}\diagdown \\ \phantom{CR9'}\diagdown_{C(R9)'-CH_2-} \\ H_2C \phantom{xx} CH_2 \phantom{xxx} (Y'') \\ \diagdown N+ \diagup \\ R7' \phantom{x} R8' \end{array} \quad (XII)$$

$$\begin{array}{c} \phantom{xxx} (CH_2)k' \\ -(CH_2)t-CR9' \diagdown_{C(R9)'-CH_2-} \\ H_2C \phantom{xx} CH_2 \\ \diagdown N+ \diagup \\ R7' \phantom{x} R8' \end{array} \quad (XIII)$$

in which formulae k' and t are chosen from 0 and 1, the sum k' plus t being equal to 1; R9' is chosen from a hydrogen atom and methyl radicals; R7' and R8', which may be identical or different, are chosen from alkyl groups having from 1 to 6 carbon atoms, hydroxyalkyl groups in which the alkyl groups may have 1 to 5 carbon atoms, lower $C_1$-$C_4$ amidoalkyl groups, R7' and R8'$_8$ can be, together with the nitrogen atom to which they are attached, heterocyclic groups such as piperidyl and morpholinyl groups; R7' and R8', which may be identical or different, may, for example, denote an alkyl group having from 1 to 4 carbon atoms; $Y^-$ is an anion such as bromide, chloride, acetate, borate, citrate, tartrate, bisulphate, bisulphite, sulphate, and phosphate ions. These polymers are described for example in French Patent No. 2 080 759 and in its Certificate of Addition 2 190 406.

Among the polymers defined above, mention may be made of the dimethyldiallylammonium chloride homopolymer sold under the name MERQUAT® 100 by the company Calgon, and its homologues of low weight-average molecular mass, as well as the copolymers of diallyldimethylammonium chloride and of acrylamide, sold under the name MERQUAT®.

(10) The quaternary diammonium polymer comprising repeating units corresponding to the formula:

$$\begin{array}{c} \phantom{xx} R10' \phantom{xxxx} R12' \\ \phantom{xx} | \phantom{xxxxxx} | \\ -\!\!\!-N+\!\!-\!A1\!-\!N+\!\!-\!B1 \\ \phantom{xx} | \phantom{xxxxxx} | \\ \phantom{xx} R11' \phantom{xxxx} R13' \phantom{x} X^- \end{array} \quad (XIV)$$

in which formula (XIV):

R10', R11', R12', and R13', which may be identical or different, are chosen from aliphatic, alicyclic, and arylaliphatic radicals having from 1 to 6 carbon atoms, and lower hydroxyalkylaliphatic radicals, or alternatively R10', R11', R12', and R13', together or separately, comprise, with the nitrogen atoms to which they are attached, at least one heterocycle optionally comprising a second heteroatom other than nitrogen, or alternatively R10', R11', R12', and R13' are chosen from linear and branched $C_1$-$C_6$ alkyl radicals substituted with at least one of nitrile groups, ester groups, acyl groups, amide groups, and groups —CO—O—R14'-D and —CO—NH—R14'-D where R14' is an alkylene and D is a quaternary ammonium group;

A1 and B1 are chosen from polymethylene groups having from 2 to 6 carbon atoms which may be linear or branched, saturated or unsaturated, and which may comprise, linked to or intercalated in the main chain, at least one aromatic ring and at least one of oxygen atoms, sulphur atoms, and sulphoxide, sulphone, disulphide, amino, alkylamino, hydroxyl, quaternary ammonium, ureido, amide, and ester groups, and $X^-$ denotes an anion derived from an acid chosen from inorganic and organic acids;

A1, R10', and R12' can form, with the two nitrogen atoms to which they are attached, a piperazine ring; in addition, if A1 is chosen from linear and branched, saturated and unsaturated alkylenes and hydroxyalkylene radicals, B1 can denote a group —$(CH_2)_{n1}$—CO-D1-OC—$(CH_2)_{n1}$— in which n1 ranges from 1 to 100, such as from 1 and 50, and D1 is chosen from:

a) a glycol residue of formula: —O-Z3-O—, where Z3 is chosen from linear and branched hydrocarbon-based radicals and groups corresponding to the following formulae:

—$(CH_2$—$CH_2$—$O)_{x'}$—$CH_2$—$CH_2$—

—$[CH_2$—$CH(CH_3)$—$O]_{y'}$—$CH_2$—$CH(CH_3)$— where x' and y' denote an integer ranging from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y3-NH—, where Y3 is chosen from linear and branched hydrocarbon-based radicalss and the divalent radical —$CH_2$—$CH_2$—S—S—$CH_2$—$CH_2$—; and d) a ureylene group of formula: —NH—CO—NH—.

$X^-$ may be an anion such as chloride and bromide.

These polymers generally have a number-average molecular mass ranging from 1,000 to 100,000.

Polymers of this type are described for example in French Patent Nos. 2 320 330, 2 270 846, 2 316 271, 2 336 434, and 2 413 907 and U.S. Pat. Nos. 2,273,780; 2,375,853; 2,388, 614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; and 4,027,020.

It is also possible to use polymers that comprise repeating units corresponding to the following formula (XV):

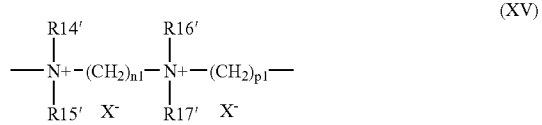

in which R14', R15', R16', and R17', which may be identical or different, are chosen from alkyl radicals and hydroxyalkyl radicals having from 1 to 4 carbon atoms; n1 and p1 are chosen from integers ranging from 2 to 20 ; and $X^-$ is an anion derived from an acid chosen from inorganic and organic acids.

(11) Polyquaternary ammonium polymers consisting of repeating units of formula (XVI):

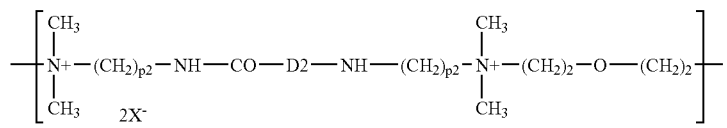

in which:

p2 denotes an integer ranging from 1 to 6;

D2 is chosen from zero (i.e., a direct bond) and groups $—(CH_2)_{r3}—CO—$ in which r3 is a number chosen from 4 and 7; and $X^-$ is an anion derived from an acid chosen from organic and inorganic acids.

The cationic polymers comprising units of formula (XVI) are described for example in patent application EP A 122 324 and can be prepared by the processes described in U.S. Pat. Nos. 4,157,388; 4,390,689; 4,702,906; and 4,719,282.

Among these, mention may be made of those having a molecular mass, measured by carbon 13 NMR, of less than 100,000, and in whose formula:

p2 is 3, and a) D2 is a group $—(CH_2)_4—CO—$, X is a chlorine atom, the molecular mass measured by carbon 13 NMR ($^{13}C$ NMR) being 5,600; a polymer of this type is sold by the company Miranol under the name MIRAPOL®-AD1;

b) D2 is a group $—(CH_2)_7—CO—$, X is a chlorine atom, the molecular mass measured by carbon 13 NMR ($^{13}C$ NMR) being 8,100; a polymer of this type is proposed by the company Miranol under the name MIRAPOL®I-AZ1;

c) D is the value zero (i.e., a direct bond), X is a chlorine atom, the molecular mass measured by carbon 13 NMR ($^{13}C$ NMR) being 25,500; a polymer of this type is sold by the company Miranol under the name MIRAPOL®-A15, or d) a block copolymer formed of units corresponding to the polymers described in paragraphs a) and c), proposed by the company Miranol under the names MIRAPOL®-9, with a $^{13}C$ NMR molecular mass of 7,800), MIRAPOL®-175, with a $^{13}C$ NMR molecular mass of 8,000, and MIRAPOL®-95, with a $^{13}C$ NMR molecular mass of about 12,500.

In another embodiment, the polymer with units of formula (XVI) in which p2 is 3, D2 denotes the value zero, and X denotes a chlorine atom, the molecular mass measured by carbon 13 NMR ($^{13}C$ NMR) is 25,500.

(12) Quaternary polymers of vinylpyrrolidone and of vinylimidazole, such as, for example, the products sold under the names LUVIQUAT® FC 905, FC 550, and FC 370 by the company BASF.

(13) Polyamines such as POLYQUART® H sold by Henkel, which is given under the reference name Polyethylene glycol (15) tallow polyamine in the CTFA dictionary.

(14) Crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- and copolymerization being followed by crosslinking with an unsaturated olefenic compound, such as methylenebisacrylamide. A crosslinked acrylamide/methacryloyloxyethyltrimethylammonium chloride copolymer, comprising 20% and 80% by weight, respectively, in the form of a dispersion comprising 50% by weight of the said copolymer in mineral oil may be used. This dispersion is sold under the name SALCARE® SC 92 by the company Allied Colloids. A crosslinked methacryloyloxyethyltrimethylammonium chloride homopolymer comprising 50% by weight of the homopolymer in mineral oil or in a liquid ester can also be used. These dispersions are sold under the names SALCARE® SC 95 and SALCARE® SC 96 by the company Allied Colloids.

Other cationic polymers which can be used according to the present disclosure are polyalkyleneimines, such as polyethyleneimines, polymers comprising units chosen from vinylpyridine and vinylpyridinium units, condensates of polyamines and of epichlorohydrin, quaternary polyureylenes, and chitin derivatives.

Among all the cationic polymers which may be used in the context of the present disclosure, mention may be made of the polymers of families (1), (9), (10), (11), (12), and (14), and for example the polymers comprising repeating units of formulae (W) and (U) below:

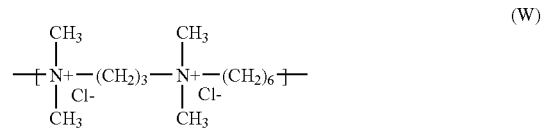

and those whose molecular weight, determined by gel permeation chromatography, ranges from 9,500 to 9,900;

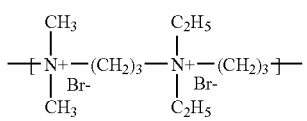
(U)

and those whose molecular weight, determined by gel permeation chromatography, is 1,200.

The concentration of cationic polymer in the composition disclosed herein may range from 0.01% to 10% by weight relative to the total weight of the composition, for example from 0.05% to 5% or from 0.1% to 3%.

Amphoteric Polymers

The amphoteric substantive polymers that may be used in accordance with certain embodiments of the present disclosure may be chosen from polymers comprising units K and M randomly distributed in the polymer chain, in which K denotes a unit derived from a monomer comprising at least one basic nitrogen atom, and M denotes a unit derived from an acidic monomer comprising at least one of carboxylic and sulphonic groups, or alternatively K and M may denote groups derived from monomers chosen from zwitterionic carboxybetaine and sulphobetaine monomers;

K and M may also denote a cationic polymer chain comprising at least one of primary, secondary, tertiary, and quaternary amine groups, in which at least one of the amine groups bears a group chosen from carboxylic and sulphonic groups linked via a hydrocarbon-based radical, or alternatively K and M may form part of a chain of at least one polymer comprising an α,β-dicarboxylic ethylene unit in which one of the carboxylic groups has been made to react with a polyamine comprising at least one of primary and secondary amine groups.

The amphoteric polymers corresponding to the above definition that may be used are chosen from the following polymers:

(1) polymers resulting from the copolymerization of a monomer derived from a vinyl compound bearing a carboxylic group such as, acrylic acid, methacrylic acid, maleic acid, α-chloroacrylic acid, and a monomer derived from a substituted vinyl compound comprising at least one basic atom, such as, dialkylaminoalkyl methacrylate and acrylate, dialkylaminoalkylmethacrylamide and -acrylamide. Such compounds are described in U.S. Pat. No. 3,836,537. Mention may also be made of the sodium acrylate/acrylamidopropyltrimethylammonium chloride copolymer sold under the name POLYQUART® KE 3033 by the company Henkel.

The substituted vinyl compound comprising at least one basic atom may also be a dialkyldiallylammonium salt such as dimethyidiallylammonium chloride. The copolymers of acrylic acid and of the latter monomer are sold under the names MERQUAT® 280, MERQUAT® 295, and MERQUAT® Plus 3330 by the company Calgon.

(2) Polymers comprising units derived from:
  a) at least one monomer chosen from acrylamides and methacrylamides substituted on the nitrogen with an alkyl radical;
  b) at least one acidic comonomer comprising at least one reactive carboxylic group; and
  c) at least one basic comonomer such as esters comprising at least one of primary, secondary, tertiary, and quaternary amine substituents of acrylic and methacrylic acids and the product of quaternization of dimethylaminoethyl methacrylate with a group chosen from dimethyl and diethyl sulphates.

The N-substituted acrylamides or methacrylamides according to certain embodiments are groups in which the alkyl radicals have from 2 to 6 carbon atoms, for example N-ethylacrylamide, N-tert-butylacrylamide, and the corresponding methacrylamides.

The acidic comonomers may be chosen from acrylic acid, methacrylic acid, crotonic acid, itaconic acid, maleic acid, fumaric acid, and alkyl monoesters, having 1 to 4 carbon atoms, of maleic acids, maleic anhydrides, fumaric acids, andfumaric anhydrides.

Basic comonomers according to certain embodiments disclosed herein may be chosen from aminoethyl, butylaminoethyl, N,N'-dimethylaminoethyl, and N-tert-butylaminoethyl methacrylates.

The copolymers whose CTFA (4th edition, 1991) name is octylacrylamide/acrylates/butylaminoethyl methacrylate copolymer such as the products sold under the names AMPHOMER® and LOVOCRYL®47 by the company National Starch may be used.

(3) Crosslinked and alkylated polyamino amides partially or totally derived from polyamino amides of general formula:

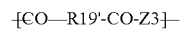 (XVII)

in which R19' is chosen from divalent radicals derived from saturated dicarboxylic acid, mono- and dicarboxylic aliphatic acids having at least one ethylenic double bond, esters of a lower alkanol having 1 to 6 carbon atoms with these acids, and radicals derived from the addition of any one of the said acids to an amine chosen from bis (primary) and bis(secondary) amines, and Z3 is chosen from bis(primary), mono- and bis(secondary) polyalkylene-polyamine radicals, and may represent:

a) in proportions ranging from 60 to 100 mol %, the radical

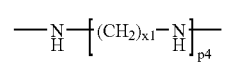 (XVIII)

where x1 is 2 and p4 is chosen from 2 and 3, or alternatively x1 is 3 and p4 is 2, this radical being derived from a compound chosen from diethylenetriamine, triethylenetetraamine, and dipropylenetriamine;

b) in proportions ranging from 0 to 40 mol %, the radical (XVIII) above in which x1 is 2 and p4 is 1 and which is derived from ethylenediamine, or the radical deriving from piperazine:

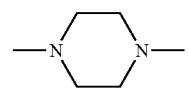

c) in proportions ranging from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides, and bis-unsaturated derivatives, using from 0.025 to 0.35 mol of crosslinking agent per amine group of the polyamino amide and alkylated by the action of a compound chosen from acrylic acids, chloroacetic acids, alkane sultones, and salts thereof.

The saturated carboxylic acids may be chosen from acids having 6 to 10 carbon atoms, such as adipic acid, 2,2,4-trimethyladipic acid, 2,4,4-trimethyladipic acid, terephthalic acid and acids comprising at least one ethylenic double bond such as, for example, acrylic acid, methacrylic acid, and itaconic acid.

The alkane sultones used in the alkylation may be chosen from propane sultone and butane sultone, and the salts of the alkylating agents may be chosen from sodium and potassium salts.

(4) Polymers comprising zwitterionic units of formula (XX):

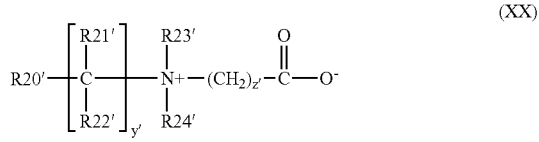

(XX)

in which R20' is chosen from polymerizable unsaturated groups such as acrylate, methacrylate, acrylamide, and methacrylamide groups, y' and z' are chosen from integers ranging from 1 to 3, R21' and R22' are chosen from a hydrogen atom, methyl, ethyl, and propyl, R23' and R24' are chosen from a hydrogen atom and alkyl radicals such that the sum of the carbon atoms in R23' and R24' does not exceed 10.

The polymers comprising such units can also comprise units derived from non-zwitterionic monomers such as dimethyl and diethylaminoethyl acrylate and methacrylate and alkyl acrylates and methacrylates, acrylamides and methacrylamides, and vinyl acetate.

By way of example, mention may be made of the copolymer of butyl methacrylate/dimethyl-carboxymethylammonioethyl methacrylate such as the product sold under the name Diaformer Z301 by the company Sandoz.

(5) Polymers derived from chitosan, described for example in French Patent No. 2 137 684 or U.S. Pat. No. 3,879,376, comprising together in their chain monomer units corresponding to formulae (XXI), (XXII) and (XXIII) below:

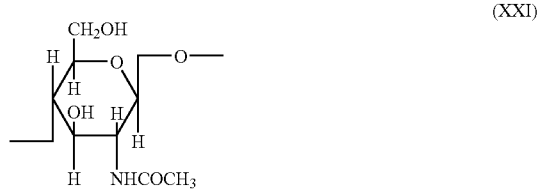

(XXI)

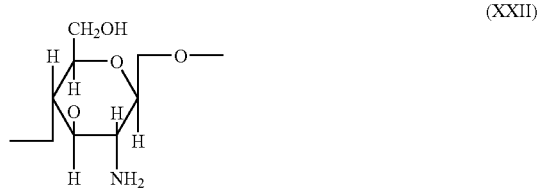

(XXII)

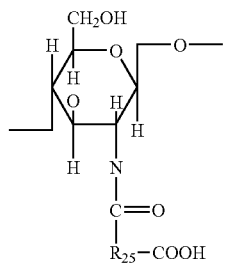

(XXIII)

the unit (XXI) being present in proportions ranging from 0 to 30%, the unit (XXII) in proportions ranging from 5 and 50%, and the unit (XXIII) in proportions ranging from 30 to 90%, it being understood that, in this unit (XXIII), $R_{25}$ represents a radical of formula:

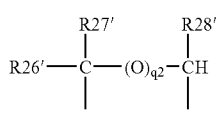

in which q2 is chosen from zero and 1;

if q2 is 0, R26', R27', and R28', which may be identical or different, are chosen from a hydrogen atom, methyl, hydroxyl, acetoxy, and amino residues, monoalkylamine residues, dialkylamine residues which are optionally interrupted by at least one nitrogen atom and optionally substituted with at least one of amine, hydroxyl, carboxyl, alkylthio, and sulphonic groups, alkylthio residues in which the alkyl group bears an amino residue, at least one of the radicals R26', R27', and R28' being, in this case, a hydrogen atom;

or, if q2 is 1, R26', R27', and R28' each represent a hydrogen atom, as well as the salts formed by these compounds with bases or acids.

Other embodiments disclosed herein of polymers of this type may comprise from 0% to 20% by weight of units (XXI), ranging from 40% to 50% by weight of units (XXII) and from 40% to 50% by weight of units (XXIII) in which $R_{25}$ is the radical —$CH_2$—$CH_2$—.

(6) Polymers derived from the N-carboxyalkylation of chitosan, such as N-carboxymethylchitosan and N-carboxybutylchitosan sold under the name Evalsan by the company Jan Dekker.

(7) Polymers corresponding to the general formula (XXIV) as described, for example, in French Patent No. 1 400 366:

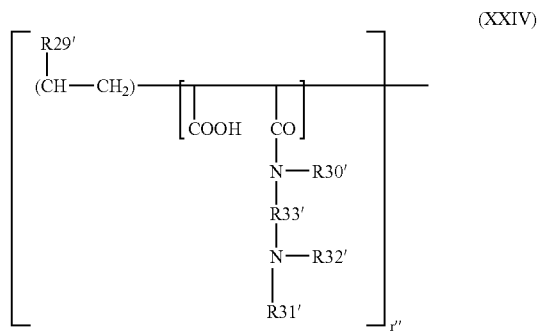

(XXIV)

in which R29' is chosen from a hydrogen atom, $CH_3O$, $CH_3CH_2O$, and a phenyl radical;

R30' is chosen from a hydrogen atom and lower alkyl radicals such as methyl and ethyl;

R31' is chosen from a hydrogen atom and lower alkyl radicals such as methyl and ethyl;

R32' is chosen from lower alkyl radicals such as methyl and ethyl, radicals corresponding to the formula: —R33'—N(R31')$_2$, wherein R33' is chosen from —$CH_2$—$CH_2$—, —$CH_2$—$CH_2$—$CH_2$—, and —$CH_2$—$CH(CH_3)$— groups, and R31' having the meanings mentioned above, as well as the higher homologues of these radicals and comprising up to 6 carbon atoms, r" is such that the molecular weight ranges from 500 to 6,000,000, such as from 1,000 to 1,000,000.

(8) Amphoteric polymers of the type -D3-X3-D3-X3- chosen from:

a) polymers obtained by the action of an acid chosen from chloroacetic acid and sodium chloroacetate on compounds comprising at least one unit of formula:

-D3-X3-D3-X3-D3-    (XXV)

where D3 denotes a radical

and X3 is chosen from the symbols E and E'; E and E', which may be identical or different, are chosen from divalent radicals which are alkylene radicals with straight or branched chains having up to 7 carbon atoms in the main chain, which is unsubstituted or substituted with at least one hydroxyl group and which can comprise, in addition to at least one of oxygen, nitrogen, and sulphur atoms, 1 to 3 aromatic and/or heterocyclic rings; the oxygen, nitrogen, and sulphur atoms being present in the form of a group chosen from ether, thioether, sulphoxide, sulphone, sulphonium, alkylamine, and alkenylamine groups, hydroxyl, benzylamine, amine oxide, quaternary ammonium, amide, imide, alcohol, ester, and urethane groups;

b) polymers of formula:

-D3-X3-D3-X3-    (XXVI)

where D3 denotes a radical

and X3 is chosen from the symbols E and E" and at least once E"; E having the meaning given above and E" being a divalent radical which is an alkylene radical with a straight or branched chain having up to 7 carbon atoms in the main chain, which is unsubstituted or substituted with at least one hydroxyl radical and comprising at least one nitrogen atom, the nitrogen atom being substituted with an alkyl chain which is optionally interrupted by at least one oxygen atom and necessarily comprising at least one carboxyl function and/or and at least one hydroxyl function and betainized by reaction with a compound chosen from chloroacetic acid and sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

The amphoteric polymers that may be mentioned according to certain embodiments are those of family (1).

As disclosed herein, the amphoteric substantive polymers may be present in an amount ranging from 0.01% to 10% by weight, such as from 0.05% to 5% by weight or from 0.1% to 3% by weight relative to the total weight of the composition.

The compositions of the invention may comprise at least one surfactant.

The at least one surfactant may be selected arbitrarily, alone or as mixtures, from anionic, amphoteric, non-ionic, zwitterionic, and cationic surfactants.

The surfactants which are suitable for the implementation of certain embodiments according to the present disclosure include, for example, the following:

(i) Anionic Surfactants:

As examples of anionic surfactants which can be used, alone or as mixtures, according to the present disclosure, mention may be made of salts, such as alkali metal salts, for example sodium salts, ammonium salts, amine salts, amino alcohol salts, and magnesium salts of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefinsulphonates, paraffinsulphonates; ($C_6$-$C_{24}$)alkyl sulphosuccinates, ($C_6$-$C_{24}$)alkyl ether sulphosuccinates, ($C_6$-$C_{24}$)alkylamide sulphosuccinates; ($C_6$-$C_{24}$)alkyl sulphoacetates, ($C_6$-$C_{24}$) acyl sarcosinates, and ($C_6$-$C_{24}$)acyl glutamates. It is also possible to use the carboxylic esters of ($C_6$-$C_{24}$)alkyl polyglycosides, such as alkylglucoside citrates, alkylpolyglycoside tartrates and alkylpolyglycoside sulphosuccinates, alkylsulphosuccinamates; acyl isethionates and N-acyltaurates, the alkyl and acyl radicals of all of these various compounds for example having from 12 to 20 carbon atoms, and the aryl radicals for example being chosen from phenyl and benzyl groups. Among the anionic surfactants which can also be used, mention may also be made of fatty acid salts such as the salts of oleic, ricinoleic, palmitic, and stearic acids, coconut oil acid and hydrogenated coconut oil acid; acyl lactylates in which the acyl radicals have 8 to 20 carbon atoms. Alkyl-D-galactosideuronic acids and their salts, polyoxyalkylenated ($C_6$-$C_{24}$)alkyl ether carboxylic acids, polyoxyalkylenated ($C_6$-$C_{24}$)alkyl aryl ether carboxylic acids, polyoxyalkylenated ($C_6$-$C_{24}$)alkylamido ether carboxylic acids and their salts, such as those having from 2 to 50 alkylene oxide, for example ethylene oxide groups, and mixtures thereof can also be used.

(ii) Non-Ionic Surfactants:

The non-ionic surfactants are also compounds that are well known per se. See in this respect "Handbook of Surfactants" by M. R. Porter, published by Blackie & Son (Glasgow and London), 1991, pp. 116-178. As disclosed herein, their nature may not be a critical feature. Thus, they may be selected from polyethoxylated and polypropoxylated alkylphenols, alpha-diols and alcohols having a fatty chain having, for example, 8 to 18 carbon atoms, it being possible for the number of ethylene oxide or propylene oxide groups to range from 2 to 50. Mention may also be made of copolymers of ethylene oxide and of propylene oxide, condensates of ethylene oxide and of propylene oxide with fatty alcohols; polyethoxylated fatty amides having from 2 to 30 mol of ethylene oxide, polyglycerolated fatty amides comprising on average 1 to 5, such as 1.5 to 4, glycerol groups; oxyethylenated fatty acid esters of sorbitan having from 2 to 30 mol of ethylene oxide; fatty acid esters of sucrose, fatty acid esters of polyethylene glycol, alkyl polyglycosides, N-alkylglucamine derivatives, amine oxides such as ($C_{10}$-$C_{14}$)alkylamine oxides and N-acylaminopropylmorpholine oxides. It will be noted that alkyl polyglycosides are non-ionic surfactants which should be mentioned.

(iii) Amphoteric and Zwitterionic Surfactants:

The amphoteric or zwitterionic surfactants, whose nature is not a critical feature as disclosed herein, can be chosen from aliphatic secondary and tertiary amine derivatives in which the aliphatic radical is a linear or branched chain having 8 to 18 carbon atoms and comprising at least one water-solubilizing anionic group, for example carboxylate, sulphonate, sulphate, phosphate, and phosphonate; mention may also be made of ($C_8$-$C_{20}$)alkylbetaines, sulphobetaines, ($C_8$-$C_{20}$)alkylamido($C_1$-$C_6$)alkylbetaines, and ($C_8$-$C_{20}$)alkylamido($C_1$-$C_6$)alkylsulphobetaines.

Among the amine derivatives, mention may be made of the products sold under the name MIRANOL®, as described in U.S. Pat. Nos. 2,528,378 and 2,781,354 and classified in the CTFA dictionary, 3rd edition, 1982, under the names Amphocarboxyglycinates and Amphocarboxypropionates of respective structures:

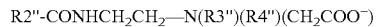

in which: R2" is chosen from linear and branched ($C_5$-$C_{20}$) alkyl radicals of, for example, an acid R2"-COOH present in a group chosen from hydrolysed coconut oil, and heptyl, nonyl, and undecyl radicals, R3" denotes a beta-hydroxyethyl group, and R4" denotes a carboxymethyl group; and

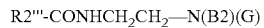

in which:

B2 is —$CH_2CH_2OX4$, G is —$(CH_2)_{z'}Y4$, wherein z' is chosen from 1 and 2;

X4 is chosen from —$CH_2CH_2$—COOH and a hydrogen atom;

Y4 is chosen from —COOH and —$CH_2$—CHOH—$SO_3H$; and

R2''' is chosen from linear and branched, saturated and unsaturated, ($C_5$-$C_{20}$) alkyl radicals of an acid R2'''-COOH present, for example, in coconut oil or in hydrolysed linseed oil, alkyl radicals, such as $C_7$, $C_9$, C11, and $C_{13}$ alkyl radicals, $C_{17}$ alkyl radicals and its iso form, and unsaturated $C_{17}$ radicals.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, and Cocoamphodipropionic acid.

By way of example, mention may be made of the cocoamphodiacetate sold under the trade name MIRANOL® C2M concentrate by the company Rhodia Chimie.

(iv) Cationic Surfactants:

Among the cationic surfactants, mention may be made of: primary, secondary, and tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium and alkylpyridinium chlorides or bromides; imidazoline derivatives; and cationic amine oxides.

The amounts of surfactants present in the compositions disclosed herein may range from 0.01% to 40%, such as from 0.5% to 30% by weight relative to the total weight of the composition.

The compositions disclosed herein may further comprise at least one non-associative rheology modifier such as cellulosic thickeners, for example hydroxyethylcellulose, hydroxypropylcellulose, and carboxymethylcellulose, guar gum and its derivatives, such as hydroxypropylguar, gums of microbial origin, such as xanthan gum and scleroglucan gum, and synthetic thickeners such as crosslinked homopolymers of acrylic acid and of acrylamidopropanesulphonic acid.

The supplementary thickener may be present in an amount ranging from 0.01% to 10% by weight relative to the total weight of the composition.

The medium of the composition, which is suitable for dyeing, may be an aqueous medium comprising water and may comprise at least one cosmetically acceptable organic solvent such as, for example, alcohols such as ethyl alcohol, isopropyl alcohol, benzyl alcohol and phenylethyl alcohol, and polyols and polyol ethers such as, for example, ethylene glycol monomethyl, monoethyl and monobutyl ether, propylene glycol and its ethers such as, for example, propylene glycol monomethyl ether, butylene glycol, dipropylene glycol, and also diethylene glycol alkyl ethers such as, for example, diethylene glycol monoethyl ether and monobutyl ether.

The at least one solvent may then be present in concentrations ranging from 0.5% to 20%, such as from 2% to 10% by weight, relative to the total weight of the composition.

The composition (A) may also comprise an effective amount of at least one additional agent, known previously elsewhere in oxidation dyeing, such as various common adjuvants, for instance sequestrants such as EDTA and etidronic acid, UV screening agents, waxes, volatile or non-volatile, cyclic, linear or branched silicones, which are optionally organically modified (in particular with amine groups), preservatives, ceramides, pseudoceramides, vegetable, mineral oils, synthetic oils, vitamins, and provitamins, for instance panthenol.

The said composition may also comprise at least one of reducing agents and antioxidants. These agents may be chosen from sodium sulphite, thioglycolic acid, thiolactic acid, sodium bisulphite, dehydroascorbic acid, hydroquinone, 2-methylhydroquinone, tert-butylhydroquinone and homogentisic acid, and, in this case, they are generally present in amounts ranging from 0.05% to 1.5% by weight relative to the total weight of the composition.

Needless to say, a person skilled in the art will take care to select the optional additional compound(s) mentioned above such that the advantageous properties intrinsically associated with the dye composition disclosed herein are not, or are not substantially, adversely affected by the envisaged addition(s).

In the ready-to-use composition or in the composition (B), the oxidizing agent may be chosen from urea peroxide, alkali metal bromates, and ferricyanides, and persalts such as perborates and persulphates. In one embodiment, hydrogen peroxide may be used. This oxidizing agent advantageously comprises an aqueous hydrogen peroxide solution whose titre may range from 1 to 40 volumes, such as from 5 to 40 volumes.

Oxidizing agents that may also be used include at least one redox enzyme such as laccases, peroxidases, and 2-electron oxidoreductases, such as uricase, where appropriate in the presence of their respective donor or co-factor.

The pH of the ready-to-use composition applied to the keratin fibers, i.e., the composition resulting from mixing together the dye composition (A) and the oxidizing composition (B), may range from 4 to 11, such as from 6 to 10, and it may be adjusted to the desired value using acidifying or basifying agents that are well known in the art in the dyeing of keratin fibers.

Among the basifying agents which may be mentioned, for example, are aqueous ammonia, alkali metal carbonates, alkanolamines such as monoethanolamine, diethanolamine and triethanolamine and derivatives thereof, oxyethylenated and oxypropylenated hydroxyalkylamines and ethylenediamines, sodium hydroxide, potassium hydroxide and the compounds of the following formula (XXVII):

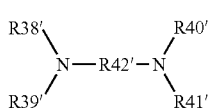
(XXVII)

in which R42' is chosen from propylene residues optionally substituted by at least one group chosen from a hydroxyl and $C_1$-$C_4$ alkyl radicals; R38', R39', R40', and R41', which may be identical or different, are chosen from a hydrogen atom, $C_1$-$C_4$ alkyl radicals, and $C_1$-$C_4$ hydroxyalkyl radicals.

The acidifying agents are chosen from, for example, mineral and organic acids, for instance hydrochloric acid, orthophosphoric acid, carboxylic acids, for instance tartaric acid, citric acid, lactic acid, and sulphonic acids.

The dyeing process disclosed herein may comprise applying the ready-to-use composition, prepared at the time of use from the compositions (A) and (B) described above, to wet or damp keratin fibers, and in leaving the composition to act for a waiting time ranging from 1 to 60 minutes, such as from 10 to 45 minutes, in rinsing the fibers and then in optionally washing the fibers with shampoo, then rinsing them again and drying them.

One variant of this process comprises applying an above-described composition and a composition comprising at least one oxidizing agent sequentially with a time delay or simultaneously to wet or damp keratin fibers, with an optional intermediate rinse, and in leaving the said compositions to act for an exposure time ranging from 1 to 60 minutes and then in rinsing the fibers, and then optionally in washing the fibers with shampoo, then rinsing them again and drying them.

The example which follows is intended to illustrate the present disclosure.

The following composition was prepared (amounts given in percentages by weight):

| | |
|---|---|
| Mixture of linear $C_{18}$ to $C_{24}$ alcohols ($C_{18}/C_{20}/C_{22}/C_{24}$: 7/57/30/6; alcohol content >95%) | 3 |
| Oxyethylenated (2EO) stearyl alcohol | 4.5 |
| Oxyethylenated (21EO) stearyl alcohol | 1.75 |
| Oleic acid | 2.6 |
| Fatty-chain cationic polyurethane obtained by condensing 1,3-bis(isocyanatomethylcyclohexane), N,N-dimethylethanolamine quaternized with bromododecane, N,N-dimethylethanolamine and polyoxyethylene of molecular weight 10,000 | 0.2 |
| Crosslinked polyacrylic acid | 0.4 |

| -continued | | |
|---|---|---|
| Hydroxypropylmethylcellulose | | 0.2 |
| Stearic acid monoethanolamide | | 3 |
| MERQUAT ® 100 in 40% strength aqueous solution | | 4 |
| Cationic polymer of formula (W) | | 2 |
| Propylene glycol | | 2 |
| Sodium metabisulphite | | 0.71 |
| EDTA (ethylenediaminetetraacetic acid) | | 0.2 |
| Tert-butylhydroquinone | | 0.3 |
| 1,4-diaminobenzene | | 0.2 |
| Para-aminophenol | | 1.2 |
| 1,3-dihydroxybenzene | | 0.1 |
| 1-hydroxy-3-aminobenzene | | 0.2 |
| 1-methyl-2-hydroxy-4-β-hydroxyethylaminobenzene | | 0.8 |
| Monoethanolamine | | 1 |
| Aqueous ammonia containing 20% $NH_3$ | | 11 |
| Perfume | q.s. | |
| Demineralized water | q.s. | 100 |

This composition was mixed at the time of use with an oxidizing composition in the form of an emulsion comprising as oxidizing agent 7.5% of hydrogen peroxide, in a proportion of 1 part by weight of dye composition per 1.5 parts by weight of oxidizing composition. The resulting mixture was applied to locks of natural hair containing 90% white hairs and was left to act for 30 minutes. After rinsing, washing with shampoo and drying, hair was obtained which was dyed in a sustained coppery red light chestnut shade.

What is claimed is:

1. A composition for the oxidation dyeing of keratin fibers comprising, in a medium suitable for dyeing,
    a) at least one oxidation dye;
    b) at least one non-oxyalkylenated fatty alcohol
    c) at least one associative polymer; and
    d) at least one amide of an alkanolamine and a $C_{14}$-$C_{30}$ fatty acid,
wherein the ratio by weight of the at least one amide of an alkanolamine and a $C_{14}$-$C_{30}$ fatty acid to the at least one associative polymer ranges from 5 to 20.

2. The composition according to claim 1, wherein the keratin fibers are human keratin fibers.

3. The composition according to claim 2, wherein the human keratin fibers are hair.

4. The composition according to claim 1, wherein the at least one amide of an alkanolamine and a $C_{14}$-$C_{30}$ fatty acid is present in the composition in an amount ranging from 0.1% to 10% by weight, relative to the total weight of the composition.

5. The composition according to claim 4, wherein the at least one amide of an alkanolamine and a $C_{14}$-$C_{30}$ fatty acid is present in the composition in an amount ranging from 1% to 5% by weight, relative to the total weight of the composition.

6. The composition according to claim 1, wherein the at least one non-oxyalkylenated fatty alcohol is chosen from lauryl, cetyl, stearyl, oleyl, behenyl, linoleyl, undecylenyl, palmitoleyl, arachidonyl, and erucyl alcohols, and mixtures thereof.

7. The composition according to claim 1, wherein the at least one non-oxyalkylenated fatty alcohol is present in the composition in an amount ranging from 0.1% to 20% by weight, relative to the total weight of the composition.

8. The composition according to claim 7, wherein the at least one non-oxyalkylenated fatty alcohol is present in the composition in an amount ranging from 1% to 10% by weight, relative to the total weight of the composition.

9. The composition according to claim 1, wherein the at least one oxidation dye is chosen from oxidation bases and couplers.

10. The composition according to claim 9, wherein the oxidation dye comprises at least one oxidation base.

11. The composition according to claim 10, wherein the at least one oxidation base is chosen from ortho- and para-phenylenediamines, double bases, ortho- and para-aminophenols, heterocyclic bases, and the acid addition salts thereof.

12. The composition according to claim 11, wherein the para-phenylenediamines are chosen from compounds of formula (I):

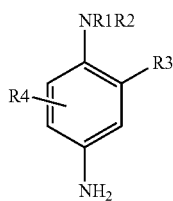

(I)

wherein:
- R1 is chosen from a hydrogen atom, $C_1$-$C_4$ alkyl radicals, $C_1$-$C_4$ monohydroxyalkyl radicals, $C_2$-$C_4$ polyhydroxyalkyl radicals, $(C_1$-$C_4)$alkoxy$(C_1$-$C_4)$alkyl radicals, and $C_1$-$C_4$ alkyl radicals substituted with at least one of nitrogenous, phenyl and 4'-aminophenyl groups;
- R2 is chosen from a hydrogen atom, $C_1$-$C_4$ alkyl radicals, $C_1$-$C_4$ monohydroxyalkyl radicals, $C_2$-$C_4$ polyhydroxyalkyl radicals, $(C_1$-$C_4)$alkoxy$(C_1$-$C_4)$alkyl radicals, and $C_1$-$C_4$ alkyl radicals substituted with at least one nitrogenous group;
- R1 and R2 may also form, together with the nitrogen atom to which they are attached, a 5- or 6-membered nitrogen heterocycle optionally substituted with at least one of alkyl, hydroxyl, and ureido groups;
- R3 is chosen from a hydrogen atom, halogen atoms, $C_1$-$C_4$ alkyls, sulpho radicals, a carboxyl radical, $C_1$-$C_4$ monohydroxyalkyl radicals, $C_1$-$C_4$ hydroxyalkoxy radicals, acetylamino$(C_1$-$C_4)$alkoxy radicals, mesylamino$(C_1$-$C_4)$alkoxy radicals, and carbamoylamino $(C_1$-$C_4)$alkoxy radicals; and
- R4 is chosen from a hydrogen atom, halogen atoms, and $C_1$-$C_4$ alkyl radicals.

13. The composition according to claim 11, wherein the double bases are chosen from compounds of formula (II):

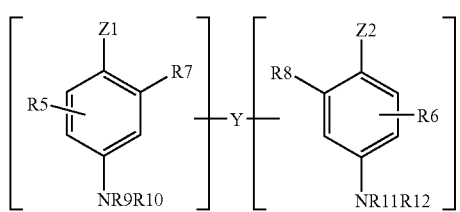

(II)

wherein:
- Z1 and Z2, which may be identical or different, are chosen from a hydroxyl and —$NH_2$ optionally substituted with at least one of $C_1$-$C_4$ alkyl radicals and a linker arm Y; the linker arm Y is chosen from linear and branched alkylene chains having from 1 to 14 carbon atoms, optionally interrupted by and optionally terminated with at least one of a nitrogenous group and a heteroatom, and optionally substituted with at least one radical chosen from hydroxyl and $C_1$-$C_6$ alkoxy radicals;
- R5 and R6 are chosen from a hydrogen atom, halogen atoms, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals, and a linker arm Y; and
- R7, R8, R9, R10, R11 and R12, which may be identical or different, are chosen from a hydrogen atom, a linker arm Y, and $C_1$-$C_4$ alkyl radicals;
- it being understood that the compounds of formula (II) comprise only one linker arm Y per molecule.

14. The composition according to claim 11, wherein the para-aminophenols are chosen from compounds of formula (III) below:

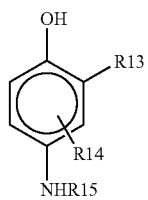

(III)

in which:
- R13 is chosen from a hydrogen atom, halogen atoms, $C_1$-$C_4$ alkyl radicals, $C_1$-$C_4$ monohydroxyalkyl radicals, $(C_1$-$C_4)$alkoxy$(C_1$-$C_4)$alkyl radicals, $C_1$-$C_4$ aminoalkyl radicals, and hydroxy$(C_1$-$C_4)$alkylamino$(C_1$-$C_4)$alkyl radicals;
- R14 is chosen from a hydrogen atom, halogen atoms, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals, $C_1$-$C_4$ cyanoalkyl radicals, and $(C_1$-$C_4)$alkoxy $(C_1$-$C_4)$alkyl radicals; and
- R15 is chosen from a hydrogen atom and $C_1$-$C_4$ alkyl radicals.

15. The composition according to claim 11, wherein the heterocyclic bases are chosen from pyridine derivatives, pyrimidine derivatives, and pyrazole derivatives.

16. The composition according to claim 9, wherein the at least one oxidation base is present in an amount ranging from 0.0005% to 12% by weight, relative to the total weight of the composition.

17. The composition according to claim 16, wherein the at least one oxidation base is present in an amount ranging from 0.005% to 8% by weight, relative to the total weight of the composition.

18. The composition according to claim 9, wherein the at least one coupler is chosen from meta-phenylenediamines, meta-aminophenols, meta-diphenols, heterocyclic couplers, and the acid addition salts thereof.

19. The composition according to claim 9, wherein the at least one coupler is present in an amount ranging from 0.0001% to 10% by weight, relative to the total weight of the composition.

20. The composition according to claim 19, wherein the at least one coupler is present in an amount ranging from 0.005% to 5% by weight, relative to the total weight of the composition.

21. The composition according to claim 11, wherein the acid addition salts of the at least one oxidation base are chosen from hydrochlorides, hydrobromides, sulphates, tartrates, lactates, and acetates.

22. The composition according claim 1, further comprising at least one direct dye.

23. The composition according to claim 1, wherein the at least one associative polymer is chosen from non-ionic, anionic, cationic, and amphoteric associative polymers.

24. The composition according to claim 23, wherein the at least one associative polymer is a fatty-chain anionic associative polymer comprising at least one hydrophilic unit and at least one fatty-chain allyl ether unit.

25. The composition according to claim 24, wherein the at least one hydrophilic unit is chosen from ethylenic unsaturated anionic monomers.

26. The composition according to claim 25, wherein the at least one hydrophilic unit is a vinylcarboxylic acid.

27. The composition according to claim 24, wherein the at least one fatty-chain allyl ether unit is chosen from monomers of formula (IV):

$$CH_2=CR'CH_2OB_nR \quad (IV)$$

wherein:
R' is chosen from a hydrogen atom and $CH_3$;
B is an ethyleneoxy radical;
n is chosen from integers ranging from 0 to 100;
R is a hydrocarbon-based radical chosen from alkyl, arylalkyl, aryl, alkylaryl, and cycloalkyl radicals, having from 8 to 30 carbon atoms.

28. The composition according to claim 27, wherein the hydrocarbon-based radical has 10 to 24 carbon atoms.

29. The composition according to claim 28, wherein the hydrocarbon-based radical has 12 to 18 carbon atoms.

30. The composition according to claim 24, wherein the fatty-chain anionic associative polymer comprises at least one unsaturated olefinic carboxylic acid hydrophilic unit and at least one unsaturated carboxylic acid ($C_{10}$-$C_{30}$)alkyl ester hydrophobic unit.

31. The composition according to claim 30, wherein the at least one unsaturated olefinic carboxylic acid hydrophilic unit corresponds to a monomer of formula (V):

$$H_2C=\underset{R16}{C}-\underset{O}{\overset{\|}{C}}-OH \quad (V)$$

in wherein R16 is chosen from a hydrogen atom, $CH_3$, and $C_2H_5$, and in which the at least one unsaturated carboxylic acid ($C_{10}$-$C_{30}$)alkyl ester hydrophobic unit corresponds to the monomer of formula (VI):

$$H_2C=\underset{R17}{C}-\underset{O}{\overset{\|}{C}}-OR18 \quad (VI)$$

in which R17 is chosen from a hydrogen atom, $CH_3$, and $C_2H_5$, and R18 is a $C_{10}$-$C_{30}$ alkyl radical.

32. The composition according to claim 31, wherein R18 is a $C_{12}$-$C_{22}$ alkyl radical.

33. The composition according to claim 18, wherein the fatty-chain anionic associative polymer is a maleic anhydride/$C_{30}$-$C_{38}$ α-olefin/alkyl maleate terpolymer.

34. The composition according to claim 18, wherein the fatty-chain anionic associative polymer is an acrylic terpolymer comprising:
(a) 20% to 70% by weight of at least one carboxylic acid containing α,β-monoethylenic unsaturation;
(b) 20% to 80% by weight of at least one non-surfactant monomer containing α,β-monoethylenic unsaturation and being other than (a); and
(c) 0.5% to 60% by weight of at least one non-ionic monourethane which is the product of reaction of at least one monohydric surfactant with at least one monoisocyanate containing monoethylenic unsaturation.

35. The composition according to claim 18, wherein the fatty-chain anionic associative polymer is chosen from copolymers comprising among their monomers at least one carboxylic acid containing α,β-monoethylenic unsaturation and at least one ester of carboxylic acid containing α,β-monoethylenic unsaturation and of oxyalkylenated fatty alcohol.

36. The composition according to claim 23, wherein the at least one associative polymer is a non-ionic fatty-chain associative polymer, and is chosen from:
(1) celluloses modified with groups comprising at least one fatty chain;
(2) hydroxypropylguars modified with groups comprising at least one fatty chain;
(3) polyurethane polyethers comprising in their chain polyoxyethylenated hydrophilic blocks and hydrophobic blocks which are chosen from aliphatic sequences, cycloaliphatic sequences, and aromatic sequences;
(4) copolymers of vinylpyrrolidone and of fatty-chain hydrophobic monomers;
(5) copolymers of a compound chosen from $C_1$-$C_6$ alkyl methacrylates and acrylates and of amphiphilic monomers comprising at least one fatty chain;
(6) copolymers of a compound chosen from hydrophilic methacrylates and acrylates and of hydrophobic monomers comprising at least one fatty chain; and
(7) polymers with at least one aminoplast ether skeleton comprising at least one fatty chain.

37. The composition according to claim 36, wherein the polyurethane polyethers comprise at least two hydrocarbon-based lipophilic chains having from 8 to 30 carbon atoms, separated by a hydrophilic block, and wherein the hydrocarbon-based chains are chosen from pendent chains and chains at the end of the hydrophilic block.

38. The composition according to claim 36, wherein the polyurethane polyethers are in multiblock form.

39. The composition according to claim 38, wherein the polyurethane polyethers are in triblock form.

40. The composition according to claim 23, wherein the at least one associative polymer is a cationic polymer comprising at least one fatty chain, and is chosen from:
(i) quaternized celluloses modified with groups comprising at least one fatty chain;
(ii) quaternized hydroxyethylcelluloses modified with groups comprising at least one fatty chain;
(iii) cationic polyurethanes;
(iv) cationic polyvinyllactams; and
(v) acrylic terpolymers comprising acrylates, amino (meth)acrylates, and $C_{10}$-$C_{30}$ alkyl itaconate, polyoxyethylenated with 20 mol of ethylene oxide.

41. The composition according to claim 40, wherein the alkyl groups of the quaternized celluloses and hydroxyethylcelluloses have from 8 to 30 carbon atoms.

42. The composition according to claim 40, wherein the cationic amphiphilic polymer is a quaternized hydroxyethylcellulose modified with a group chosen from $C_{12}$ and $C_{18}$ alkyl groups.

43. The composition according to claim 40, wherein the cationic amphiphilic polyurethane is a polymer of formula (Ia):

$$R19\text{-}X\text{---}(P)_n\text{-}[L\text{-}(Y)_m]_r\text{-}L'\text{-}(P')_p\text{---}X'\text{---}R20 \qquad (Ia)$$

wherein:
R19 and R20, which may be identical or different, are chosen from hydrophobic groups and a hydrogen atom;
X and X', which may be identical or different, are chosen from groups comprising an amine function optionally bearing at least one of hydrophobic groups and the groups L";
L, L', and L", which may be identical or different, are a group derived from a diisocyanate;
P and P', which may be identical or different, are a group comprising an amine function optionally bearing at least one hydrophobic group;
Y is chosen from hydrophilic groups;
r is chosen from integers ranging from 1 to 100; and
n, m, and p, which may be identical or different, each range from 0 to 1000; wherein
the polymer of formula (Ia) comprises at least one amine function chosen from protonated and quaternized amine functions and at least one hydrophobic group.

44. The composition according to claim 23, wherein the at least one amphoteric polymer comprises at least one fatty chain having 8 to 30 carbon atoms and at least one non-cyclic cationic unit.

45. The composition according to claim 44, wherein the at least one associative polymer is an amphoteric polymer comprising from 1 to 20 mol % of monomer comprising at least one fatty chain, relative to the total number of moles of monomers.

46. The composition according to claim 44, wherein the at least one amphoteric polymer comprises:
1) at least one monomer chosen from formula (Ia) and (Ib):

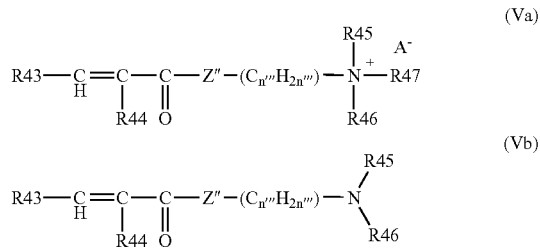

in which
R43 and R44, which may be identical or different, are chosen from a hydrogen atom and a methyl radical;
R45, R46, and R47, which may be identical or different, are chosen from linear and branched alkyl radicals having from 1 to 30 carbon atoms;
Z" is chosen from an NH group and an oxygen atom;
n'" is chosen from integers ranging from 2 to 5; and
$A^-$ is an anion derived from an acid chosen from organic and mineral acids;

2) at least one monomer of formula (VI)

in which R48 and R49, which may be identical or different, are chosen from a hydrogen atom and a methyl radical; and 3) at least one monomer of formula (VII):

in which
R48 and R49, which may be identical or different, are chosen from a hydrogen atom and a methyl radical;
X'" is chosen from oxygen and nitrogen atoms; and
R50 is chosen from linear and branched alkyl radicals having from 1 to 30 carbon atoms; wherein
at least one of the monomers chosen from formulae (Va), (Vb), and (VII) comprises at least one fatty chain.

47. The composition according to claim 46, wherein the monomers chosen from formulae (Va) and (Vb) are chosen from dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, and dimethylaminopropylacrylamide, which are optionally quaternized.

48. The composition according to claim 46, wherein the monomer of formula (Va) is chosen from acrylamidopropyltrimethylammonium chloride and methacrylamidopropyltrimethylammonium chloride.

49. The composition according to claim 46, wherein the monomer of formula (VI) is chosen from acrylic acid, methacrylic acid, crotonic acid, and 2-methylcrotonic acid.

50. The composition according to claim 46, wherein the monomer of formula (VII) is chosen from $C_{12}$-$C_{22}$ alkyl acrylates and methacrylates.

51. The composition according to claim 50, wherein the monomer of formula (VII) is chosen from $C_{16}$-$C_{28}$ alkyl acrylates and methacrylates.

52. The composition according to claim 1, wherein the at least one associative polymer is present in the composition in an amount ranging from 0.05% to 10% by weight, relative to the total weight of the composition.

53. The composition according to claim 52, wherein the at least one associative polymer is present in the composition in an amount ranging from 0.1% to 5% by weight, relative to the total weight of the composition.

54. The composition according to claim 1, wherein the at least one associative polymer is a cationic fatty-chain polymer.

55. The composition according to claim 1, wherein the at least one associative polymer is chosen from cationic polyurethanes.

56. The composition according to claim 1, wherein the ratio by weight of the at least one amide of an alkanolamine and a $C_{14}$-$C_{30}$ fatty acid to the at least one non-oxyethylenated fatty alcohol ranges from 0.1 to 10.

57. The composition according to claim 56, wherein the ratio ranges from 0.5 to 5.

58. The composition according to claim 1, further comprising at least one substantive polymer chosen from amphoteric and cationic substantive polymers, and wherein said at least one substantive polymer is different from the at least one associative polymer.

59. The composition according to claim 58, wherein the at least one substantive polymer is a homopolymer of dimethyldiallylammonium chloride.

60. The composition according to claim 58, wherein the at least one substantive polymer is a polymer comprising repeating units of formula (W):

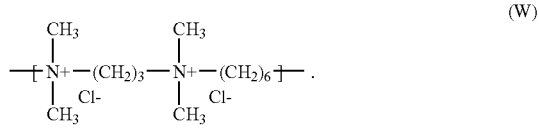

61. The composition according to claim 58, wherein the at least one substantive polymer is a polymer comprising repeating units of formula (U):

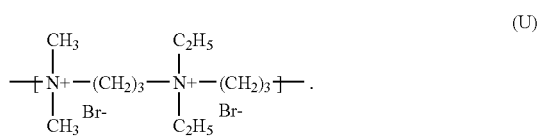

62. The composition according to claim 58, wherein the at least one substantive polymer chosen from cationic and amphoteric substantive polymers is present in an amount ranging from 0.01% to 10% by weight, relative to the total weight of the composition.

63. The composition according to claim 62, wherein the at least one substantive polymer chosen from cationic and amphoteric substantive polymers is present in an amount ranging from 0.05% to 5% by weight, relative to the total weight of the composition.

64. The composition according to claim 63, wherein the at least one substantive polymer chosen from cationic and amphoteric substantive polymers is present in an amount ranging from 0.1% to 3% by weight, relative to the total weight of the composition.

65. The composition according to claim 1, further comprising at least one surfactant chosen from anionic, amphoteric, non-ionic, zwitterionic, and cationic surfactants.

66. The composition according to claim 65, wherein the at least one surfactant is present in an amount ranging from 0.01% to 40% by weight, relative to the total weight of the composition.

67. The composition according to claim 66, wherein the at least one surfactant is present in an amount ranging from 0.5% to 30% by weight, relative to the total weight of the composition.

68. The composition according to claim 1, further comprising at least one supplementary thickener.

69. The composition according to claim 68, wherein the at least one supplementary thickener is chosen from cellulosic thickeners, guar gum derivatives, gums of microbial origin, and synthetic thickeners.

70. The composition according to claim 68, wherein the at least one supplementary thickener is present in an amount ranging from 0.01% to 10% by weight, relative to the total weight of the composition.

71. The composition according to claim 1, further comprising at least one reducing agent, present in an amount ranging from 0.05% to 1.5% by weight, relative to the total weight of the composition.

72. A ready-to-use composition for the oxidation dyeing of keratin fibers comprising, in a medium suitable for dyeing,
 a) at least one oxidation dye;
 b) at least one non-oxyalkylenated fatty alcohol;
 c) at least one associative polymer;
 d) at least one amide of an alkanolamine and a $C_{14}$-$C_{30}$ fatty acid; and
 e) at least one oxidizing agent,
wherein the ratio by weight of the at least one amide of an alkanolamine and a $C_{14}$-$C_{30}$ fatty acid to the at least one associative polymer ranges from 5 to 20.

73. The composition according to claim 72, wherein the at least one oxidizing agent is chosen from hydrogen peroxide, urea peroxide, alkali metal bromates, alkali metal ferricyanides, persalts, and redox enzymes together where appropriate with the respective donor or co-factor thereof.

74. The composition according to claim 73, wherein the at least one oxidizing agent is hydrogen peroxide.

75. The composition according to claim 74, wherein the at least one oxidizing agent is an aqueous hydrogen peroxide solution whose titre ranges from 1 to 40 volumes.

76. The composition according to claim 75, wherein the pH of the aqueous hydrogen peroxide solution ranges from 4 to 11.

77. A multi-compartment dyeing kit for the oxidation dyeing of keratin fibers, comprising at least one compartment comprising at least one oxidation dye, at least one non-oxyalkylenated fatty alcohol, at least one associative polymer, and at least one amide of an alkanolamine and a $C_{14}$-$C_{30}$ fatty acid, and
 an additional compartment comprising at least one oxidizing agent.
wherein the ratio by weight of the at least one amide of an alkanolamine and a $C_{14}$-$C_{30}$ fatty acid to the at least one associative polymer ranges from 5 to 20.

78. The composition according to claim 1, wherein the amide of an alkanolamine and a $C_{14}$-$C_{30}$ fatty acid is chosen from:
 oleic acid diethanolamide,
 myristic acid monoethanolamide,
 soya fatty acid diethanolamide,
 stearic acid ethanolamide,
 linoleic acid diethanolamide,
 oleic acid monoisopropanolamide,
 stearic acid monoethanolamide,
 behenic acid monoethanolamide,
 isostearic acid monoisopropanolamide,
 erucic acid diethanolamide, and
 ricinoleic acid monoethanolamide.

79. The composition according to claim 1, wherein the amide of an alkanolamine and a $C_{14}$-$C_{30}$ fatty acid is chosen from:
 oleic acid diethanolamide,
 myristic acid monoethanolamide,
 soya fatty acid diethanolamide,
 stearic acid ethanolamide,
 linoleic acid diethanolamide,
 stearic acid monoethanolamide,
 behenic acid monoethanolamide,
 erucic acid diethanolamide, and
 ricinoleic acid monoethanolamide.

* * * * *

UNITED STATES PATENT AND TRADEMARK OFFICE
CERTIFICATE OF CORRECTION

| | | |
|---|---|---|
| PATENT NO. | : 7,326,256 B2 | Page 1 of 1 |
| APPLICATION NO. | : 10/728888 | |
| DATED | : February 5, 2008 | |
| INVENTOR(S) | : Cottard et al. | |

It is certified that error appears in the above-identified patent and that said Letters Patent is hereby corrected as shown below:

In claim 1, column 40, line 33, "alcohol" should read --alcohol;--.

In claim 22, column 43, line 5, "according claim" should read --according to claim--.

In claim 31, column 43, line 50, "wherein" should read --which--.

In claim 72, column 48, line 11, "$C_{14}$-$C_{30}$fatty" should read --$C_{14}$-$C_{30}$ fatty--.

In claim 77, column 48, line 34, "agent." should read --agent,--.

Signed and Sealed this

Twenty-fourth Day of June, 2008

JON W. DUDAS
*Director of the United States Patent and Trademark Office*